US009730979B2

(12) United States Patent
Vitek et al.

(10) Patent No.: US 9,730,979 B2
(45) Date of Patent: *Aug. 15, 2017

(54) METHODS FOR DECREASING SET IN INHIBITING PROTEIN PHOSPHATASE 2A (PP2A) AND/OR INCREASING THE ACTIVITY OF CYCLIN-DEPENDENT KINASE 5 (CDK5) BY AN APOE PEPTIDE

(75) Inventors: Michael P. Vitek, Cary, NC (US); Dale J. Christensen, Cary, NC (US); Jessica Oddo, Durham, NC (US)

(73) Assignee: COGNOSCI, INC., Research Triangle Park, NC (US)

( * ) Notice: Subject to any disclaimer, the term of this patent is extended or adjusted under 35 U.S.C. 154(b) by 1479 days.

This patent is subject to a terminal disclaimer.

(21) Appl. No.: 12/519,278

(22) PCT Filed: Dec. 21, 2007

(86) PCT No.: PCT/US2007/088600
§ 371 (c)(1),
(2), (4) Date: Dec. 18, 2009

(87) PCT Pub. No.: WO2008/080082
PCT Pub. Date: Jul. 3, 2008

(65) Prior Publication Data
US 2010/0144627 A1    Jun. 10, 2010

Related U.S. Application Data

(60) Provisional application No. 60/876,153, filed on Dec. 21, 2006, provisional application No. 60/929,750, filed on Jul. 11, 2007.

(51) Int. Cl.
| | | |
|---|---|---|
| *A61K 38/00* | (2006.01) | |
| *A61K 49/00* | (2006.01) | |
| *A61B 5/00* | (2006.01) | |
| *C07K 7/00* | (2006.01) | |
| *C07K 9/00* | (2006.01) | |
| *C07K 14/00* | (2006.01) | |
| *C07K 14/81* | (2006.01) | |
| *C07K 14/775* | (2006.01) | |
| *G01N 33/483* | (2006.01) | |
| *A61K 38/17* | (2006.01) | |

(52) U.S. Cl.
CPC ........ *A61K 38/1709* (2013.01); *C07K 14/775* (2013.01)

(58) Field of Classification Search
CPC .. C07K 14/4702; C07K 14/775; C07K 14/47; C07K 14/4738; A61K 38/00; C12Q 1/42; C12Q 1/485; C12Q 1/6883; C12Q 2600/158; C12Q 1/6837; C12Q 1/6886; C12Q 2600/112; C12Q 2600/136; G01N 2500/10; G01N 33/564; G01N 33/57426

See application file for complete search history.

(56) References Cited

U.S. PATENT DOCUMENTS

| | | | | | |
|---|---|---|---|---|---|
| 6,812,339 | B1 * | 11/2004 | Venter et al. | ............... | 536/24.31 |
| 7,947,645 | B2 * | 5/2011 | Vitek | ................... | C07K 14/775 |
| | | | | | 514/1.1 |
| 8,034,762 | B2 * | 10/2011 | Vitek | ................. | A61K 38/1709 |
| | | | | | 514/1.1 |
| 8,288,335 | B2 * | 10/2012 | Vitek | ................... | C07K 14/775 |
| | | | | | 514/1.1 |
| 8,288,336 | B2 * | 10/2012 | Vitek | ................. | A61K 38/1709 |
| | | | | | 514/1.1 |
| 8,629,242 | B2 * | 1/2014 | Vitek | ................. | A61K 38/1709 |
| | | | | | 530/300 |
| 2002/0146757 | A1 * | 10/2002 | Tang | .................. | C07K 14/8107 |
| | | | | | 435/69.1 |
| 2002/0164789 | A1 | 11/2002 | Laskowitz et al. | | |
| 2003/0165575 | A1 | 9/2003 | Iqbal et al. | | |
| 2004/0019118 | A1 | 1/2004 | Iqbal et al. | | |
| 2004/0265889 | A1 * | 12/2004 | Durham et al. | ................. | 435/6 |
| 2007/0154955 | A1 * | 7/2007 | Tseng et al. | .................... | 435/7.2 |
| 2009/0042783 | A1 * | 2/2009 | Vitek et al. | ..................... | 514/12 |

FOREIGN PATENT DOCUMENTS

| | | | | | |
|---|---|---|---|---|---|
| EP | | 2382983 | * | 2/2011 | ............. A61K 38/00 |
| WO | WO 99/45950 | A | | 9/1999 | |
| WO | WO0175067 | | * | 10/2001 | |
| WO | WO 03/026479 | A1 | | 4/2003 | |
| WO | WO 2005/082399 | | | 9/2005 | |
| WO | WO 2006029028 | A2 | * | 3/2006 | ............. A61K 38/17 |

OTHER PUBLICATIONS

Fukukawa et al. International J. Oncol. 2005, 26: 751-756.*
Tsi et al. Mol. Pharmacol. 2002, 101: 90-101.*
Burgess et al. J of Cell Bio. 1990, 111:2129-2138.*
Bowie et al. Science, 1990, 247:1306-1310.*
Pawson et al. 2003, Science 300:445-452.*
Madeira et al., "SET protein (TAF1β, I2PP2A) is involved in neuronal apoptosis induced by an amyloid precursor protein cytoplasmic subdomain," FASEB Journal, vol. 19: 1905-1907, 2005.
Li et al., "The myeloid leukemia-associated protein SET is a potent inhibitor of protein phosphatase 2A," J. Biol. Chem., vol. 271: 11059-11062, 1996.

(Continued)

*Primary Examiner* — Chang-Yu Wang
(74) *Attorney, Agent, or Firm* — Cooley LLP

(57) ABSTRACT

The present invention provides methods for modulating SET activity by contacting SET with a binding agent such as an ApoE peptide derivative. In one embodiment of the invention, a pharmaceutical composition capable of modulating SET activity is administered to a patient for the treatment of an inflammatory or neurological condition. In another embodiment of the invention, compounds efficacious for the treatment of inflammatory and neurological conditions are identified by screening for a binding agent capable of competing with or inhibiting the binding of an ApoE derivative to SET.

12 Claims, 13 Drawing Sheets

(56) References Cited

OTHER PUBLICATIONS

Zhu et al., "Alterations in activities of protein phosphatases PP1 and PP2A in T and B lymphocytes of autoimmune MRL/MpJ-lpr/lpr mice," J. Biochem., vol. 114: 50-54, 1993.

Wang et al., "Apolipoprotein E (ApoE) peptide regulates tau phosphorylation via two different signaling pathways," Journal of Neuroscience Research, vol. 51: 658-665, 1998.

Tanimukai et al., "Up-regulation of inhibitors of protein phosphatase-2A in Alzheimer's Disease," American Journal of Pathology, vol. 166: 1761-1771, 2005.

Chohan et al., "Involvement of $I_2^{PP2A}$ in the abnormal hyperphosphorylation of tau and its reversal by Memantine," vol. 580: 3973-3979, 2006.

Swope, International Search Report and Written Opinion, Sep. 29, 2008.

Li et al., "Apolipoprotein E-derived peptides ameliorate clinical disability and inflammatory infiltrates into the spinal cord in a murine model of multiple sclerosis," Journal of Pharmacology and Experimental Therapeutics, vol. 318, No. 3, Sep. 1, 2003, pp. 956-965.

Laskowitz et al.: "Apolipoprotein E-derived peptides reduce CNS inflammation: implications for therapy of neurological disease," Acta Neurologica Scandinavica, vol. 114, No. s185, Aug. 1, 2006, pp. 15-20.

Lynch et al., "A novel therapeutic derived from apolipoprotein E reduces brain inflammation and improves outcome after closed head injury," Experimental Neurology, vol. 192, No. 1, Mar. 1, 2005, pp. 106-116.

Lynch et al., "APOE genotype and an ApoE-mimetic peptide modify the systemic and central nervous system inflammatory response," Journal of Biological Chemistry, vol. 278, No. 49, Dec. 5, 2003, pp. 48529-48533.

Laskowitz et al., "Downregulation of microglial activation by apolipoprotein E and apoE-mimetic peptides," Experimental Neurology, vol. 167, No. 1, Jan. 1, 2001, pp. 74-85.

N. Canela, "The SET Protein Regulates G2/M Transition by Modulating Cyclin B-Cyclin-dependent Kinase 1 Activity," Journal of Biological Chemistry, vol. 278, No. 2, Jan. 3, 2003, pp. 1158-1164.

* cited by examiner

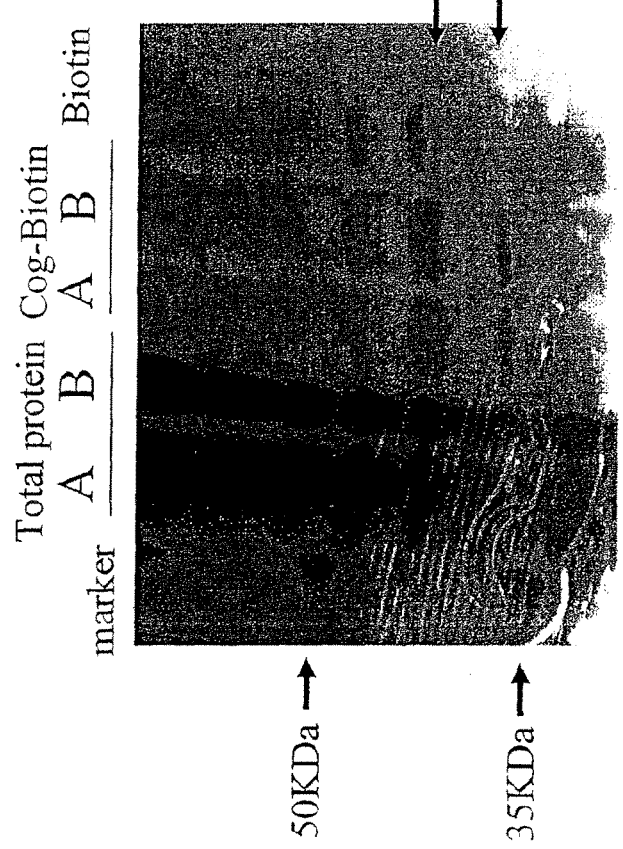

Figure 2
Cog-biotin interact to SET protein directly

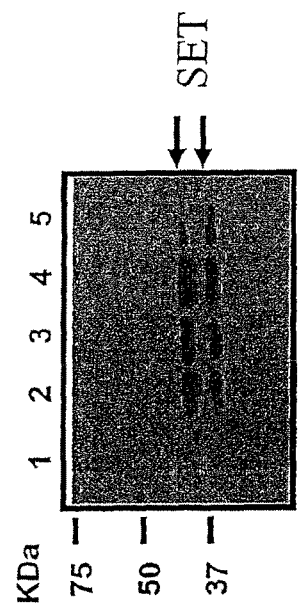

1... pull down with biotin from total protein
2... pull down with biotin-Cog133 from total protein
3... pull down with biotin-Cog133 from total protein+Cog133(20x)
4... pull down with biotin-Cog133 from total protein+ pep96 (20x)
5... pull down with biotin-Cog133 from total protein+ pep1410 (20x)

| peptide # | sequence | MTT LD50(uM) | NITRITE EC50(uM) | N/MTT EC50(uM) |
|---|---|---|---|---|
| Pep96 | Ac-ASHLRKLRKRLL-CONH2 | NA | NA | NA |
| Pep1410 | Ac-AS-Aib-LRKL-Aib-KRLL-NH2 | 18 | 2.5 | 2.5 |

FIGURE 9
A
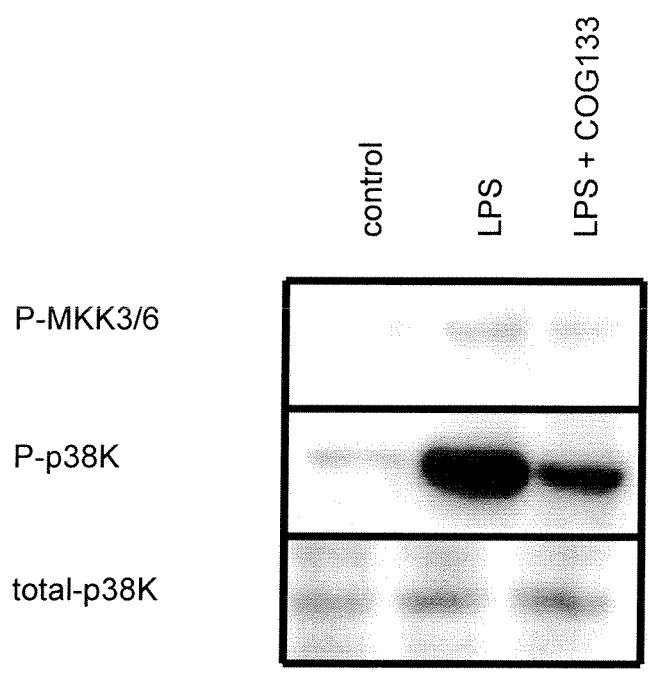
B
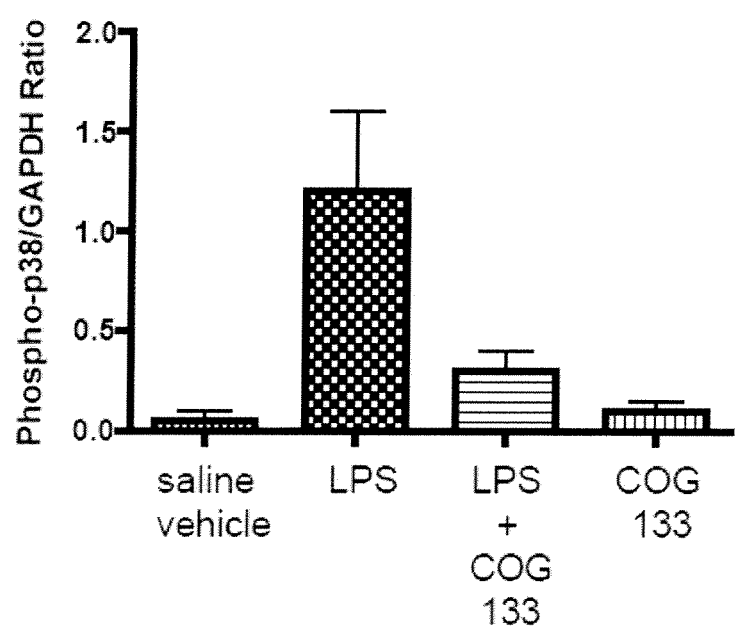

FIGURE 11
A
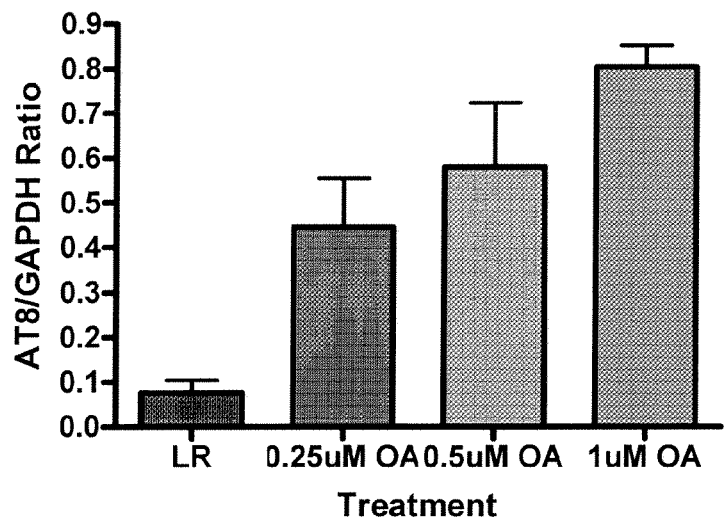
B
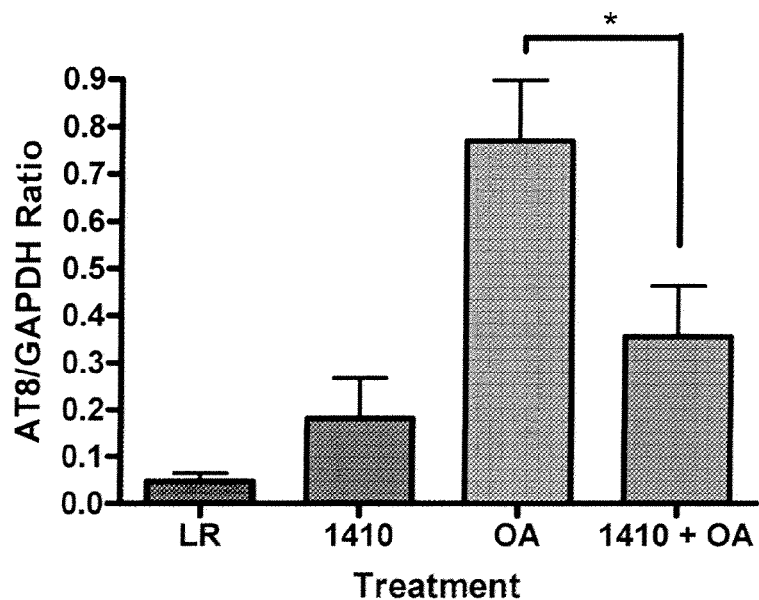

SEQUENCE LISTING

<160> NUMBER OF SEQ ID NOS: 4

<210> SEQ ID NO 1
<211> LENGTH: 17
<212> TYPE: PRT
<213> ORGANISM: Unknown
<220> FEATURE:
<223> OTHER INFORMATION: COG133 peptide composed of residues 133-149 of apoE

<400> SEQUENCE: 1

Leu Arg Val Arg Leu Ala Ser His Leu Arg Lys Leu Arg Lys Arg Leu
1               5                   10                  15

Leu

<210> SEQ ID NO 2
<211> LENGTH: 12
<212> TYPE: PRT
<213> ORGANISM: Unknown
<220> FEATURE:
<223> OTHER INFORMATION: COG1410 peptide mimetic of an apoE protein
<220> FEATURE:
<221> NAME/KEY: MISC_FEATURE
<222> LOCATION: (1)..(1)
<223> OTHER INFORMATION: May be acetylated on N-terminus
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MISC_FEATURE
<222> LOCATION: (12)..(12)
<223> OTHER INFORMATION: May be amidated on C-terminus

<400> SEQUENCE: 2

Ala Ser Xaa Leu Arg Lys Leu Xaa Lys Arg Leu Leu
1               5                   10

<210> SEQ ID NO 3
<211> LENGTH: 210
<212> TYPE: PRT
<213> ORGANISM: Mus musculus

<400> SEQUENCE: 3

Met Ser Ala Pro Thr Ala Lys Ala Ser Lys Lys Glu Leu Asn Ser Asn
1               5                   10                  15

His Asp Gly Ala Asp Glu Thr Ser Glu Lys Glu Gln Gln Glu Ala Ile
                20                  25                  30

Glu His Ile Asp Glu Val Gln Asn Glu Ile Asp Arg Leu Asn Glu Gln
            35                  40                  45

Ala Ser Glu Glu Ile Leu Lys Val Glu Gln Lys Tyr Asn Lys Leu Arg
        50                  55                  60

Gln Pro Phe Phe Gln Lys Arg Ser Glu Leu Ile Ala Lys Ile Leu Asn
65                  70                  75                  80

Phe Trp Val Thr Thr Phe Val Asn His Pro Gln Val Ser Ala Leu Leu
                85                  90                  95

Gly Glu Glu Asp Glu Glu Ala Leu His Tyr Leu Thr Arg Val Glu Val
                100                 105                 110

Thr Glu Phe Glu Asp Ile Lys Ser Gly Tyr Arg Ile Asp Phe Tyr Phe
            115                 120                 125

Asp Glu Asn Pro Tyr Phe Glu Asn Lys Val Leu Ser Lys Glu Phe His
        130                 135                 140

Leu Asn Glu Ser Gly Asp Pro Ser Ser Lys Ser Thr Glu Ile Lys Trp
145                 150                 155                 160

Lys Ser Gly Lys Asp Leu Thr Lys Arg Ser Ser Leu Thr Gln Asn Lys
                165                 170                 175

Ala Ser Arg Lys Arg Gln His Glu Glu Pro Glu Ser Phe Phe Thr Trp
            180                 185                 190

Phe Thr Ala His Ser Asp Ala Gly Ala Asp Glu Leu Gly Glu Val Ile
        195                 200                 205

Lys Asp
    210

<210> SEQ ID NO 4
<211> LENGTH: 289
<212> TYPE: PRT
<213> ORGANISM: Mus musculus

<400> SEQUENCE: 4

Met Ala Pro Lys Arg Gln Ser Ala Ile Leu Pro Gln Pro Lys Lys Pro
1               5                   10                  15

Arg Pro Ala Ala Ala Pro Lys Leu Glu Asp Lys Ser Ala Ser Pro Gly
            20                  25                  30

Leu Pro Lys Gly Glu Lys Glu Gln Gln Glu Ala Ile Glu His Ile Asp
        35                  40                  45

Glu Val Gln Asn Glu Ile Asp Arg Leu Asn Glu Gln Ala Ser Glu Glu
    50                  55                  60

Ile Leu Lys Val Glu Gln Lys Tyr Asn Lys Leu Arg Gln Pro Phe Phe
65                  70                  75                  80

Gln Lys Arg Ser Glu Leu Ile Ala Lys Ile Pro Asn Phe Trp Val Thr
                85                  90                  95

Thr Phe Val Asn His Pro Gln Val Ser Ala Leu Leu Gly Glu Glu Asp
            100                 105                 110

Glu Glu Ala Leu His Tyr Leu Thr Arg Val Glu Val Thr Glu Phe Glu
        115                 120                 125

Asp Ile Lys Ser Gly Tyr Arg Ile Asp Phe Tyr Phe Asp Glu Asn Pro
    130                 135                 140

Tyr Phe Glu Asn Lys Val Leu Ser Lys Glu Phe His Leu Asn Glu Ser
145                 150                 155                 160

Gly Asp Pro Ser Ser Lys Ser Thr Glu Ile Lys Trp Lys Ser Gly Lys
                165                 170                 175

Asp Leu Thr Lys Arg Ser Ser Gln Thr Gln Asn Lys Ala Ser Arg Lys
            180                 185                 190

Arg Gln His Glu Glu Pro Glu Ser Phe Phe Thr Trp Phe Thr Asp His
        195                 200                 205

Ser Asp Ala Gly Ala Asp Glu Leu Gly Glu Val Ile Lys Asp Asp Ile
    210                 215                 220

Trp Pro Asn Pro Leu Gln Tyr Tyr Leu Val Pro Asp Met Asp Asp Glu
225                 230                 235                 240

```
Glu Gly Glu Ala Glu Asp Asp Asp Asp Asp Glu Glu Glu Glu Gly
            245             250             255

Leu Glu Asp Ile Asp Glu Glu Gly Asp Glu Asp Glu Gly Glu Glu Asp
        260             265             270

Asp Asp Glu Asp Glu Gly Glu Glu Gly Glu Glu Asp Glu Gly Glu Asp
        275             280             285

Asp
```

METHODS FOR DECREASING SET IN INHIBITING PROTEIN PHOSPHATASE 2A (PP2A) AND/OR INCREASING THE ACTIVITY OF CYCLIN-DEPENDENT KINASE 5 (CDK5) BY AN APOE PEPTIDE

CROSS-REFERENCE TO RELATED APPLICATIONS

This application is a national phase entry of PCT/US2007/088600, filed Dec. 21, 2007, which claims priority to U.S. Provisional Application Ser. No. 60/876,153, filed Dec. 21, 2006, and U.S. Provisional Application Ser. No. 60/929,750, filed Jul. 11, 2007, which are herein incorporated by reference in their entireties.

FIELD OF THE INVENTION

The present invention provides methods for modulating SET activity by contacting SET with a binding agent. In one embodiment, the binding agent is an ApoE peptide derivative. The invention provides methods for the treatment of inflammatory and neurological conditions by modulation of SET. The invention also provides methods for identifying compounds efficacious for the treatment of inflammatory and neurological conditions.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COGO01403USSeqlistST25.txt, date recorded: Jan. 12, 2012, file size 5 kilobytes).

BACKGROUND

SET, also known as protein phosphatase 2A inhibitor 2 protein ($I_2^{PP2A}$), putative HLA-DR associated protein II (PHAPII), inhibitor of granzyme A-activated protein II (IGAAD) and template-activating factor (TAF1β), was first described as part of the SET-CAN fusion gene in a patient with acute undifferentiated leukemia, apparently as a result of a gene translocation (Von Lindern et al., 1992, Mol. Cell. Biol. 12: 3346-3355). SET has since been characterized as a multifunctional protein that protects histones from acetylation by histone acetyl transferases, modulates HuR mRNA binding, regulates G2/M transition via binding to p21CIP1, and acts as a transcription factor for P450c17 activation (Seo et al., 2001, Cell. 104: 119-130; Brennan et al., 2000, J. Cell Biol. 151: 1-14; Canela et al., 2003, J. Biol. Chem. 278: 1158-1164; Compagnone et al., 2000, Mol. Endocrinol. 14: 875-888).

More recently, it has been suggested that SET plays a role in Alzheimer's disease (AD) and other neurodegenerative diseases (Madeira et al., 2005, FASEB J. 19: 1905-1907; Tsujio et al., 2005, FEBS Letters. 579: 363-372). Evidence of such SET activity includes a finding of increased SET expression in the hippocampus of AD patients which correlates positively with neurofibrillary tangles and negatively with Mini-Mental Status Exam (Blalock et al., 2004, Proc. Natl. Acad. Sci. U.S.A. 101: 2173-2178). SET has also been found to play an important role in the regulation of cell death induced by a pro-apoptotic domain of the amyloid precursor protein (APP), a protein seen in the brains of AD patients (Madeira et al., 2005, FASEB J. 19: 1905-1907). When overexpressed, the short cytoplasmic domain of APP referred to as "Jcasp" activates caspase-3 and induces neuronal death. SET specifically binds to Jcasp, and down-regulation of SET reduces Jcasp-induced cell death. Conversely, SET gain of function increases cell death.

Although much still needs to be done to elucidate the role of SET in neurological diseases, SET has been found to be a potent inhibitor of protein phosphatase 2A (PP2A), a phosphatase involved in the regulation of diverse cellular processes (Li et al., 1996, J. Biol. Chem. 271: 11,059-11,062). The inhibition of PP2A by SET appears to be substrate specific. It has been demonstrated that SET inhibits PP2A when using phosphorylated myelin basic protein as a substrate but does not inhibit the activity of PP2A when using phosphorylated casein as the substrate (Guo et al. 1995, Biochemistry, 34, 1988). PP2A appears to be deactivated by phosphorylation and activated by methylation of its C subunit (Chen et al., 1992, Science. 257, 1261-1264; Guo and Damuni, 1993, Proc. Natl. Acad. Sci. U.S.A. 90: 2500-2504; Favre et al., 1994, J. Biol. Chem. 269: 16311-16317).

PP2A dephosphorylates tau and MAP2 in vitro (Yamamoto et al., 1988, J. Neurochem. 50: 1614-1623). Tau proteins belong to the family of microtubule-associated proteins. They are mainly expressed in neurons where they play an important role in the assembly of tubulin monomers into microtubules and stabilize neuronal microtubule networks. Microtubules are involved in maintaining the cell shape and serve as tracks for axonal transport. Tau proteins also establish some links between microtubules and other cytoskeletal elements or proteins. Their expression is developmentally regulated by an alternative splicing mechanism, and six different isoforms exist in the human adult brain. Further, tau proteins are the major constituents of intraneuronal and glial fibrillar lesions described in Alzheimer's disease and numerous neurodegenerative disorders referred to as tauopathies. Molecular analysis has revealed that an abnormal phosphorylation of tau might be one of the important events in the process leading to their detachment from microtubules, aggregation into filamentous structures and/or stabilization of filamentous structures comprising paired helical filaments and/or neurofibrillary tangles (Buee et al., 2000, Brain Res. Rev. 33: 95-130).

The activities of PP2A are believed to be compromised in Alzheimer's disease brain. In AD brain, it has been speculated that PP2A deficiency permits hyperphosphorylation of tau leading to neurofibrillary tangle formation and neuronal degeneration. Evidence supporting this hypothesis includes the finding that in vitro treatment of metabolically active rat brain slices with okadaic acid causes inhibition of PP2A activity and abnormal hyperphosphorylation of tau resulting in the inability of tau to bind to microtubules (Gong et al., 1995, J. Neurochem. 65: 732-738). As described above, SET is overexpressed in the hippocampus of Alzheimer's patients relative to normal people. The observed in vivo overexpression would result in inhibition of PP2A, in a manner similar to okadaic acid, and would be expected to lead to hyperphosphorylated tau and neurofibrillary tangle formation. It has also been reported that phosphorylation at a site, which is recognized by PP2A, is required for trafficking of β-secretase to the surface of cells where it is active in cleavage of the amyloid precursor protein (APP) (Walter et al. 2001, J Biol Chem. 276, 14634). Cleavage of APP by β-secretase initiates a proteolytic pathway that results in the production of amyloid-β (Aβ) protein. Further, as described above, methylation of PP2A is required for full activity. Treatment with S-adenosylhomocysteine leads to decreased methylation of PP2A, reduces PP2A activity, and has been shown to result in increased production of Aβ due to increases in phosphorylation of the soluble APP that leads to β cleavage (Sontag et al., 2007, J. Neurosci. 27: 2751-2759). Therefore, activation of PP2A may reduce the level of Aβ in the brains of Alzheimer's patients by preventing the trafficking of the secretase to the surface or by decreasing the phosphorylation that targets APP towards β cleavage that is required for Aβ formation.

PP2A has also been shown to interact with, and dephosphorylate a number of proteins involved in the signal transduction cascades that propagate inflammatory signaling processes. One such protein is the Inhibitor of NFκB kinase (IκK). IκK is activated by phosphorylation, and in turn phosphorylates the Inhibitor of NFκB (IκB) (Hong et al. 2007 *J. Biol. Chem.*) Phosphorylation of IκB results in release of Nuclear Factor κB (NFκB) from the inactive IκB:NFκB complex and the degradation of IκB. This leaves NFκB free to become phosphorylated and translocated to the nucleus where it acts as a transcription factor that controls gene expression of pro-inflammatory cytokines Activation of NFκB has also been shown to be required in the process of antigen presentation (Yoshimura et al. *Scan. J. Immunol.* 58, 165), a process that is integral to innate immunity and autoimmune disorders.

PP2A has also been reported to bind to and dephosphorylate the p38 mitogen activated protein kinase (MAPK), thus inactivating it (Sundaresan & Farndale 2002 FEBS Letters 528, 139). Activation of p38 and other MAPKs is required for production of pro-inflammatory cytokines and T-cell proliferation. Another protein implicated in inflammatory signaling that may be dephosphorylated by PP2A is IL-1beta receptor-associated kinase (IRAK). IRAK is integral in interleukin signaling and signaling cascades stemming from the Toll-like receptor family proteins.

Apolipoprotein E (ApoE) is another protein that has been shown to play an important role in neurological disease and has immunomodulatory properties. ApoE has been demonstrated to have immunomodulatory effects in vitro, including suppression of lymphocyte proliferation and immunoglobulin synthesis after mitogenic challenge. ApoE is secreted in large quantities by macrophages after peripheral nerve injury, and by microglia, astrocytes and oligodendrocytes (glial cells) after CNS injury.

Human ApoE is found in three major isoforms: ApoE2, ApoE3, and ApoE4; these isoforms differ by amino acid substitutions at positions 112 and 158. The most common isoform is ApoE3, which contains cysteine at residue 112 and arginine at residue 158; ApoE2 is the least common isoform and contains cysteine at residues 112 and 158; ApoE4 contains arginine at residues 112 and 158. Additional rare sequence mutations of human ApoE are known (see, e.g., Weisgraber, 1994, *Advances in Protein Chemistry* 45:249, 268-269).

It has been observed that ApoE influences development of late onset and familial AD. This effect is robust and dose-dependent, such that homozygous individuals with an APOE4/4 genotype have an approximately 20-fold increased risk of developing AD, and heterozygous individuals with an APOE3/4 genotype have a 4-fold increased risk relative to patients who are homozygous for the most common APOE3/3 genotype (Strittmatter et al., 1993; Corder et al., 1993; reviewed by Laskowitz et al., 1998a). This observation has led to a resurgence of interest in the function of ApoE in the mammalian central nervous system (CNS). Because of its association with AD, multiple laboratories have examined interactions between ApoE and proteins believed to play a role specific to the pathogenesis of AD. Further, several laboratories have described isoform-specific interactions between ApoE and Abeta or ApoE and tau (Strittmatter et al. 1994; Gallo et al. 1994; Fleming et al. 1996; reviewed by Laskowitz et al., 1998a). The role of ApoE in the CNS, however, remains undefined, and it is unclear which or any of these interactions are relevant in human neurodegenerative disease.

It has previously been found that certain ApoE peptide derivatives are useful for treating inflammation and neurological disorders including traumatic brain injury (TBI). In this regard, U.S. application Ser. No. 10/252,120, filed Sep. 23, 2002 (herein incorporated by reference in its entirety), discloses methods of using ApoE analogs, including COG 133, to treat or ameliorate the neurological effects of cerebral ischemia or cerebral inflammation. COG 133 is a small peptide, comprised of residues 133-149 of the ApoE protein. U.S. Application No. 60/606,506, filed Sep. 2, 2004, and U.S. Application No. 60/608,148, filed Sep. 9, 2004 (herein incorporated by reference in their entireties), disclose the use of COG 133, COG 1410 and other ApoE derivatives to treat traumatic brain injury and diseases involving inflammation. COG 1410 is a mutated derivative of COG 133 that exhibits a 4-fold gain in therapeutic window and a 7.4-fold gain in Therapeutic Index as compared to COG 133.

Despite recent efforts in elucidating the role of SET in neurological disease, there has not previously been an identified connection between SET and ApoE. The present inventors have surprisingly found that COG 133 and other ApoE derivative peptides bind to and modulate the activity of the SET protein. The present invention thus provides a novel method of modulating PP2A activity by blocking SET binding to PP2A using exogenous agents such as ApoE derivatives. The present invention also provides methods of modulating other activities of SET, including enhancement of Cdk5 activity and increased Jcasp-induced neuronal apoptosis, by interfering with SET binding to those respective targets. Such novel methods can be used for the treatment of neurological, inflammatory, and other diseases as well as for screening drug candidates for efficacy in the treatment of neurological, inflammatory, and other diseases.

SUMMARY OF THE INVENTION

The present invention provides a method of modulating an activity of SET comprising contacting SET or SET variant with an exogenous agent capable of binding SET or SET variant. Depending on the activity of SET, the activity of SET may be increased or decreased by binding SET with an agent according to the present invention. For instance, modulation of SET by contact with an agent of the invention can cause a decrease in phosphorylation of p38 MAP kinase, a decrease in LPS-induced nitric oxide, an increase or decrease in PP2A phosphatase activity, a decrease in Jcasp induced cell death and/or a decrease in neuronal cell death. Binding of SET with an agent of the invention may also result in an inhibition of abnormal tau hyperphosphorylation, reversion of a leukemic phenotype, inhibition of antigen presentation, or inhibition of T-cell proliferation.

The agent of the present invention can be a peptide such as an ApoE analog. In one embodiment of the invention, the agent is COG 133 (SEQ ID NO: 1). In another embodiment, the agent is a COG 133 derivative such as COG 1410 (SEQ ID NO: 2) which provides a longer therapeutic window for the treatment, enhanced efficacy, improved blood brain barrier transport, and/or a greater therapeutic index. Other ApoE analogs useful in the present invention are described in U.S. Application Nos. 60/606,506 and 60/608,148, which are herein incorporated by reference in their entireties.

In one embodiment, the ApoE analog can contain SEQ ID NO: 1 or SEQ ID NO: 2 or any of the derivatives described in described in U.S. Application Nos. 60/606,506 and 60/608,148 linked to one to five additional amino acids or amino acid analogs at the N-terminus or C-terminus or both the N-terminus and C-terminus, wherein such additional amino acids do not adversely affect the ability of the peptide to modulate SET activity. The agent peptide containing SEQ ID NO: 1 or SEQ ID NO: 2 or other ApoE derived peptide can contain 12 amino acids or more, 13 amino acids or more, 17 amino acids or more, 18 amino acids or more, 20 amino acids or more, 30 amino acids or more or 40 amino acids or more. In one embodiment, the agent peptide consists essentially of SEQ ID NO: 1 or SEQ ID NO: 2.

The present invention includes agents which compete with peptides containing the sequence of COG 133 (SEQ ID NO: 1) for binding to SET. Such agents include, but are not limited to, proteins, other peptides, small molecules, antibodies and antibody derivatives. For instance, a peptide containing COG 1410 (SEQ ID NO: 2) or COG 112 (COG 133 conjugated to antennapedia) can compete with COG 133 for binding to SET. In one embodiment, the agent inhibits the binding of the COG 133 peptide to SET.

The methods of the present invention include administering an agent capable of modulating SET to a subject for the treatment of an inflammatory, neurological, or leukemic condition. A patient diagnosed with an inflammatory, neurological, or leukemic condition can be administered a pharmaceutical composition containing an effective amount of an agent for the treatment of a wide range of neurological, inflammatory, or cancerous diseases. In one embodiment of the present invention, the patient is treated for a neurological condition associated with an increase in microglial activation, glial activation or neuronal cell death wherein administration of an agent capable of modifying SET reduces glial activation, reduces microglial activation, reduces tau hyperphosphorylation, and/or reduces neuronal cell death.

The present invention also includes a method of identifying an agent that binds to SET and modulates SET activity. According to this method, SET is contacted with at least one test agent to identify one or more agents that bind SET. Screening is performed to identify one or more agents for the ability to compete with or inhibit binding of an ApoE peptide containing SEQ ID NO: 1 or other ApoE derivative to SET. Screening can be performed by methods known in the art, including but not limited to, phage display, yeast display, or small molecule libraries using a ligand displacement assay. As a skilled artisan can appreciate, this method can be used to screen for drug candidates for any of the inflammatory, neurological and/or other conditions described herein.

BRIEF DESCRIPTION OF THE FIGURES

FIG. 1 is a Coomassie gel wherein 2 bands correlate with SET.

FIG. 2 is a western blot probed with an anti-SET antibody.

FIG. 9 depicts the effect of COG 133 on LPS-induced p38MAP kinase activation. Panel A is a representative western blot of phospho p38MAPK and its upstream activation kinase MKK3/6 from microglial cells treated with LPS alone or in the presence of COG 133. Panel B shows a densitometry analysis of western blots similar to the one shown in panel A. The phospho p38MAPK signal is normalized to the signal for GAPDH protein.

FIG. 11. (A) Okadaic acid (OA) induced phosphorylation of Tau in mouse cortex and (B) reduction in phospho-Tau by treatment of COG1410. Asterisk indicates $p<0.05$.

DETAILED DESCRIPTION OF THE INVENTION

Figure 3:
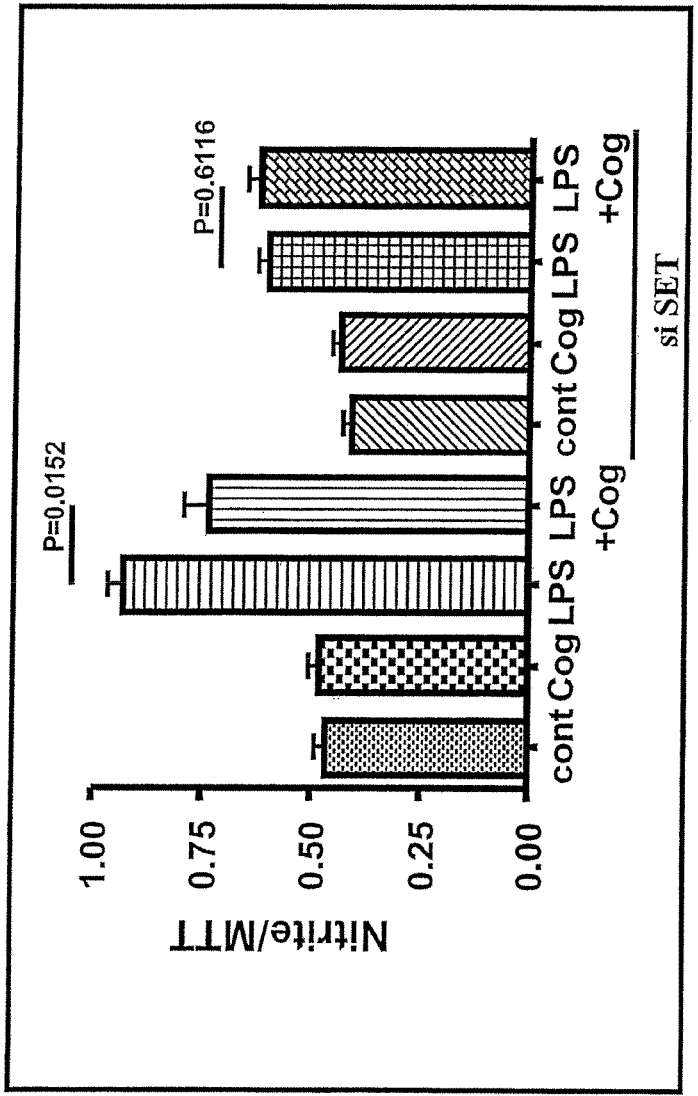
FIG. 3 is a graph showing the amount of nitric oxide produced in BV2 cells treated with COG 133, LPS, and LPS+COG 133, both with and without siRNA to SET.

The inventors of the present invention herein demonstrate that activities of SET can be modulated by contacting SET with an exogenous agent. Surprisingly, the inventors have found that ApoE analogs and agents that compete with such analogs for SET binding may be used to modulate activities of SET.

SET and ApoE are active in many biological processes associated with disease. As shown herein, ApoE derivatives are capable of modulating SET activities. As such, the inventors of the present invention propose that the methods of modulating SET described herein can be used for treatment of disorders previously only associated with ApoE. Thus, the ability to modulate SET through contact with at least one agent such as an ApoE derivative or other SET binding agent presents an avenue for treating patients suffering from a wide range of diseases including inflammatory and neurological conditions.

As used herein, "modulating" refers to changes in SET activity observed in vitro or in vivo, including an increase or decrease in SET activity. As previously discussed, SET is suspected of being involved in multiple biological processes associated with disease. For instance, SET activities have been linked to diseases such as myeloid leukemia, Alzheimer's disease and diseases associated with the induction of neuronal cell death. Known SET biological activities and SET-related processes include, but are not limited to, inhibition of protein phosphatase 2A activity (a phosphatase involved in cell cycle progression and tau dephosphorylation), enhancement of the activity of cdk5/p35 through SET association with p35 (a kinase involved in cell cycle regulation, tau phosphorylation, and neurofilament phosphorylation), increase in transcriptional activity of AP-1 and c-Jun, interaction with the Jcasp domain of APP to regulate cell death, inhibition of histone acetylation by histone acetyl transferases, modulation of HuR mRNA binding, regulation of G2/M transition via binding to p21CIP1, activation of P450c17 and repression of the expression of presenilin homologs. Modulation of SET by an exogenous agent can also result in a decrease of SET-induced neuronal cell death. The inventors of the invention have linked additional activities to SET such as the regulation of phosphorylation of p38 MAP kinase and modulation of nitric oxide (LPS-induced nitric oxide and poly I:C induced nitric oxide). In one embodiment of the present invention, modulation of SET by an exogenous agent results in a decrease in phosphorylation, i.e., decrease in activation, of p38 MAP kinase, ERK, JNK, and/or NF-κB; and/or a reduction in LPS-induced nitric oxide. Further, SET appears to play a role in the phosphorylation of tau though inhibition of PP2A activity.

Activities of SET can be either direct activities or indirect activities. A direct activity of SET occurs when SET interacts directly with a molecule and is capable of affecting the activity of the molecule though the interaction. An indirect activity of SET occurs when a molecule is affected by SET although the molecule does not directly interact with SET. For instance, downstream molecules in phosphorylation cascades such as the p38 MAP kinase cascade can be indirectly affected by SET as the result of a SET activity involving upstream proteins in the cascade.

As used herein, "capable of binding" refers to the ability of an agent to interact with SET upon coming into contact with it. Binding can be confirmed by known methods in the art including the use of IP-western blots and other hybridization-based assays as discussed in the examples section. A library of potential agents can be screened for the ability to bind SET by methods known in the art including, but not limited to, phage display, yeast display, peptide display (such as PIN technology), antibody-display, etc. The ability of an agent to inhibit the binding of a peptide to SET can likewise be determined by methods known in the art such as competitive binding assays, fluorescence polarization and the like.

As used herein, "agent" refers to any substance capable of binding to SET and modulating at least one activity of SET. Agents include, but are not limited to, nucleic acid molecules, peptides, fusion proteins, monoclonal or polyclonal antibodies or fragments thereof or chemical entities. "Exogenous" refers to anything not naturally occurring in the body. For instance, the ApoE analogs disclosed in U.S. patent application Ser. Nos. 10/252,120, 11/091,336, 60/606,506 and 60/606,507 which are herein incorporated by reference in their entireties, are exogenous agents.

In one embodiment of the present invention, the agent that binds to SET is an ApoE analog. For instance, the agent can be an analog and derivative of COG 133, a truncated peptide comprised of residues 133-149 of ApoE. This truncated ApoE peptide, referred to as COG 133 (LRVRLASHLRKL-RKRLL (SEQ. ID. NO. 1)) has previously proved useful in treating or reducing cerebral ischemia or cerebral inflammation. See U.S. application Ser. No. 10/252,120, filed Sep. 23, 2002, incorporated herein by reference in its entirety. A large number of analogs of the ApoE 130-150 peptide were previously created and their activity tested in a cell-based assay for suppression of release of inflammatory cytokines and free radicals and in receptor binding assays. Lynch et al., 2003, *J. Biol. Chem.* 278(4), 48529-33 and U.S. application Ser. No. 10/252,120, filed Sep. 23, 2002, Ser. No. 09/957,909, filed Sep. 21, 2001, and Ser. No. 09/260,430, filed Mar. 1, 1999, now abandoned, which claims the benefit of U.S. Provisional Application No. 60/077,551, filed Mar. 11, 1998, the contents of each of which are incorporated herein by reference in their entireties.

In one embodiment of the present invention, the efficacy of COG 133 and other ApoE peptide mimetics can be improved by conjugation to a protein transduction domain (PTD) as described in PCT application PCT/US05/31431, filed Sep. 2, 2005, which claims priority to U.S. Provisional Applications 60/606,506, filed Sep. 2, 2004, 60/608,148, filed Sep. 9, 2004, 60/606,507, filed Sep. 2, 2004, which are herein incorporated by reference in their entireties. PTDs are short basic peptides that promote the intracellular delivery of cargo that would otherwise fail to, or only minimally, traverse the cell membrane. PTDs can be used to enhance CNS penetration of compounds. For instance, empirical testing of PTDs can be performed to identify PTDs that are capable of transporting cargo across the blood brain barrier.

Some derivatives of COG 133 such as COG 1410 (Ac-AS-Aib-LRKL-Aib-KRLL-NH$_2$ (SEQ ID NO: 2) are capable of providing a wider therapeutic window for the treatment and prevention of neurological and inflammatory diseases. Therapeutic window refers to the time period during which the compounds of the invention can be effectively administered following the onset of a neurological or inflammatory condition. By increasing the therapeutic window, the agents of the present invention can be administered at greater time intervals following the onset of the condition.

In addition, agents such as COG 1410 are of enhanced efficacy, and demonstrate a greater therapeutic index. As used herein, "therapeutic index" refers to the maximum tolerated dose at which no animal dies divided by the minimal effective dose at which performance after injury is significantly better than saline controls.

The agents of the present invention may also provide increased CNS penetration or increase the therapeutic window for the treatment and prevention of a neurological condition. As used herein, "CNS penetration" refers to the ability of a compound, including a peptide, to cross the blood brain barrier and enter the Central Nervous System (CNS).

Without being bound to any theory, the inventors of the present invention have reason to believe that COG 133 and derivatives thereof inhibit the ability of SET to inhibit PP2A, i.e., COG 133 is an activator of PP2A. Accordingly, in one embodiment of the invention, ApoE analogs or other agents that compete with the disclosed ApoE peptides for SET binding may be used to inhibit the ability of SET to inhibit PP2A.

The present invention also includes agents that potentiate SET binding to PP2A resulting in decreased PP2A activity.

Accordingly, in one embodiment of the invention, an agent of the invention may be used to enhance the binding of SET to PP2A.

In another embodiment, the present invention provides compounds for the methods described herein and methods for identifying the same. In one aspect, the invention provides agents that are ApoE analogs. In one aspect, the invention provides agents that are α-helical peptides. Such agents can include analogs and derivatives of COG 133, a peptide of the sequence LRVRLASHLRKLRKRLL (SEQ. ID. NO. 1).

Agents of the present invention can be produced by standard techniques as are known in the art. The agents of the invention may have attached various label moieties such as radioactive labels, heavy atom labels and fluorescent labels for detection and tracing. Fluorescent labels include, but are not limited to, luciferin, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BODIPY, Cy.sup.5, etc.

In one embodiment of the invention, the agent capable of modifying SET is a peptide. Modification of the peptide agents disclosed herein to enhance the functional activities associated with these peptides could be readily accomplished by those of skill in the art. For instance, the peptides used in the methods of the present invention can be chemically modified or conjugated to other molecules in order to enhance parameters such as solubility, serum stability, etc., while retaining functional activity. In particular, the peptides of the invention may be acetylated at the N-terminus and/or amidated at the C-terminus, or conjugated, complexed or fused to molecules that enhance serum stability, including but not limited to albumin, immunoglobulins and fragments thereof, transferrin, lipoproteins, liposomes, α-2-macroglobulin and α-1-glycoprotein, PEG and dextran. Such molecules are described in detail in U.S. Pat. No. 6,762,169, which is herein incorporated by reference in its entirety.

Another variation of the peptide agents of the present invention is the linking of from one to fifteen amino acids or analogs to the N-terminal or C-terminal amino acid of the therapeutic peptide. Analogs of the peptides of the present invention can also be prepared by adding from one to fifteen additional amino acids to the N-terminal, C-terminal, or both N- and C-terminals, of an active peptide, where such amino acid additions do not adversely affect the ability of the peptide to bind to receptors at the site bound by a peptides of the invention. For instance COG 133 and COG 1410 variants can be created by adding from one to fifteen additional amino acids to the N-terminal, C-terminal, or both N- and C-terminals, of the active peptide. An active peptide is any peptide capable of binding to SET and modulating a SET activity.

The peptide agents of the present invention further include conservative variants of the peptides herein described. As used herein, a conservative variant refers to alterations in the amino acid sequence that do not adversely affect the biological functions of the peptide. A substitution, insertion or deletion is said to adversely affect the peptide when the altered sequence prevents or disrupts a biological function associated with the peptide. For example, the overall charge, structure or hydrophobic/hydrophilic properties of the peptide may be altered without adversely affecting a biological activity. Accordingly, the amino acid sequence can be altered, for example to render the peptide more hydrophobic or hydrophilic, without adversely affecting the biological activities of the peptide. Ordinarily, the conservative substitution variants, analogs, and derivatives of the peptides, will have an amino acid sequence identity to the disclosed sequences SEQ ID NOs: 1 and 2 of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the peptide agents of the present invention include molecules having the amino acid sequence disclosed in SEQ ID Nos. 1 or 2 and binding agents that compete with these peptides for SET binding; fragments thereof having a consecutive sequence of at least about 3, 4, 5, 6, 10, 15, or more amino acid residues of the therapeutic peptide; amino acid sequence variants of such peptides wherein an amino acid residue has been inserted N- or C-terminal to, or within, the disclosed sequence; and amino acid sequence variants of the disclosed sequence, or their fragments as defined above, that have been substituted by another residue. Peptide compounds comprising the peptide sequences of the invention may be between about 15, 20, 25, 30, 35, 40, 45 and 50 amino acids or more. Contemplated variants further include those containing predetermined mutations by, e.g., homologous recombination, site-directed or PCR mutagenesis, and the corresponding peptides of other animal species, including but not limited to rabbit, rat, porcine, bovine, ovine, equine and non-human primate species, and derivatives wherein the peptide has been covalently modified by substitution, chemical, enzymatic, or other appropriate means with a moiety other than a naturally occurring amino acid (for example, a detectable moiety such as an enzyme or radioisotope).

The agents capable of modulating SET, including but not limited to COG 133 and derivatives thereof, can be in free form or the form of a salt, where the salt is pharmaceutically acceptable. These include inorganic salts of sodium, potassium, lithium, ammonium, calcium, magnesium, iron, zinc, copper, manganese, and the like. Various organic salts of the agent may also be made with, including, but not limited to, acetic acid, propionic acid, pyruvic acid, maleic acid, succinic acid, tartaric acid, citric acid, benozic acid, cinnamic acid, salicylic acid, etc.

In one embodiment, the agents of the present invention are used in combination with a pharmaceutically acceptable carrier. The present invention thus also provides pharmaceutical compositions suitable for administration to a subject. Such compositions comprise an effective amount of the agent of the present invention in combination with a pharmaceutically acceptable carrier. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active agents can alternatively be formulated encapsulated in liposomes, using known methods. Additionally, the intranasal administration of peptides to treat CNS conditions is known in the art (see, e.g., U.S. Pat. No. 5,567,682, incorporated herein by reference to Pert, regarding intranasal administration of peptide T to treat AD). Preparation of a agent of the present invention for intranasal administration can be carried out using techniques as are known in the art.

Pharmaceutical preparations of the agents of the present invention can optionally include a pharmaceutically acceptable diluent or excipient.

An effective amount of the agent of the present invention is that amount that modulates an activity of SET in a subject. In one embodiment, the effective amount of an agent peptide decreases microglial activation compared to that which would occur in the absence of the agent; in other words, an amount that decreases the production of neurotoxic and neuromodulatory compounds by the microglia, compared to that which would occur in the absence of the agent. Neuromodulatory refers to a non-lethal alteration in neuron function. The effective amount (and the manner of administration) will be determined on an individual basis and will be based on the specific agent being used and a consideration of the subject (size, age, general health), the condition being treated (AD, acute head injury, cerebral inflammation, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the agents described herein can be determined using in vitro tests, animal models or other dose-response studies, as are known in the art.

An alternative method of administering peptide agents of the present invention is carried out by administering to the subject a vector carrying a nucleic acid sequence encoding the peptide, where the vector is capable of entering cells of the body such as brain cells so that the peptide is expressed and secreted. Expression of peptide agents in the brain thus make the agents available to microglial cells. Suitable vectors are typically viral vectors, including DNA viruses, RNA viruses, and retroviruses. Techniques for utilizing vector delivery systems and carrying out gene therapy are known in the art. Herpesvirus vectors, adenovirus vectors, adeno-associated virus vectors and lenti-viral vectors are particular types of vectors that can be employed in administering compounds of the present invention.

The agents of the present invention may be used alone to modulate activities of SET or in combination with other therapeutic agents with mechanisms of action not believed to be related to the modulation of SET, such as, e.g., oxygen radical scavenging agents such as superoxide dismutase (SOD) or anti-inflammatory agents such as corticosteroids, hydrocortisone, prednisone and the like; anti-diarrheal agents such as loperamide and the like, antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, gancyclovir, ribavirin, interferons and the like; analgesic agents such as salicylic acid, acetaminophen, ibuprofen, flurbiprofen, morphine and the like; local anesthetics such as lidocaine, bupivacaine, benzocaine and the like; growth factors such as colony stimulating factor, granulocyte-macrophage colony stimulating factor, and the like; antihistamines such as diphenhydramine, chlorphencramine and the like; anti-nausea medications, nutritional additives such as leukovorin, and other like substances.

The agents of the methods of the present invention may also be used in combination with anti-inflammatory cytokines, growth factors, or leukocyte migration inhibitory compounds. Useful cytokines include, but are not limited to, IL-4, IL-10, IL-11, and IL-13, particularly IL-4 and IL-10, which are known to suppress production of inflammatory cytokines and to be involved in restoring the immune system. Growth factors include GM-CSF among others. These cytokines and growth factors may be administered as purified proteins—obtained naturally or from recombinant sources—or administered in the form of nucleic acids that express these peptides, particularly as fusion proteins.

The agents of the present invention can be administered acutely (i.e., during the onset or shortly after events leading to an inflammatory or neurological condition), or can be administered prophylactically (e.g., before scheduled surgery, or before the appearance of inflammatory and/or neurological signs or symptoms), or administered during the course of a degenerative disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The typical daily regime can be from about 0.01 µg/kg body weight per day, from about 1 mg/kg body weight per day, from about 10 mg/kg body weight per day, from about 100 mg/kg body weight per day, from about 1,000 mg/kg body weight per day. Dosages can be between about 0.01 µg/kg and about 10 mg/kg body weight per day, depending on the agent, or between about 1 mg/kg and about 10 mg/kg body weight per day.

As used herein, the term "administering to the brain of a subject" refers to the use of routes of administration, as are known in the art, that provide the compound to the central nervous system tissues, and in particular the brain, of a subject being treated.

The blood-brain barrier presents a barrier to the passive diffusion of substances from the bloodstream into various regions of the CNS. However, active transport of certain agents is known to occur in either direction across the blood-brain barrier. Substances that can have limited access to the brain from the bloodstream can be injected directly into the cerebrospinal fluid. Cerebral ischemia and inflammation are also known to modify the blood-brain barrier and result in increased access to substances in the bloodstream.

Administration of an agent directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical agent into the cerebrospinal fluid ("spinal injection") is known in the art, and is suited for administration of the present agents.

Pharmacologic-based procedures are also known in the art for circumventing the blood brain barrier, including the conversion of hydrophilic compounds into lipid-soluble drugs. The active agent can be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. This method can be used so long as the second agent does not interfere in the binding of the agent to SET. Examples of suitable carriers include pyridinium, fatty acids, inositol, cholesterol, and glucose derivatives also add vitamin C. The carrier can be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 (Pardridge et al). These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198. Specific carrier molecules disclosed include hemoglobin, lysozyme, cytochrome c, ceruloplasmin, calmodulin, ubiquitin and substance P. See also U.S. Pat. No. 5,017,566 which is herein incorporated by reference in its entirety.

The present invention also provides methods of treatment by administering the agents capable of modulating SET as described above to a mammalian subject diagnosed with an inflammatory, neurological, or other condition. For instance, the compounds of the present invention can be used for the treatment of diseases including, but not limited to, multiple sclerosis, leukemia, rheumatoid arthritis, psoriasis, myelodysplastic syndrome, tuberous sclerosis, vasculitis, acute disseminated encephalomyelitis, Guillain-Barre syndrome or sepsis, acute CNS injury such as traumatic brain injury, stroke, closed head injury, global cerebral ischemia, cerebral edema, focal ischemia, subarachnoid hemorrhage, or intracranial hemorrhage, or a chronic neurological disease such as Alzheimer's disease, diseases associated with tauopathy, HIV-associated encephalopathy, neurolathyrism, amyotrophic lateral sclerosis (ALS), Huntington's chorea, Parkinson's disease, epilepsy, d-2-hydroxyglutaric aciduria or schizophrenia. In one embodiment, the methods of the present invention can be used for the amelioration of symptoms associated with central nervous system (CNS) disorders and injuries, including, but not limited to, traumatic brain injury, Alzheimer's disease (AD), diseases associated with tauopathy, cerebral ischemia, cerebral edema or the reduction of glial or microglial activation. The present invention also provides methods for the amelioration of symptoms associated with CNS trauma, inflammation or cerebral ischemia. In one embodiment, the present invention provides methods for reducing neuronal cell death or suppressing macrophage activation.

In treating CNS disorders and injuries, the blood brain barrier (BBB) drastically limits the transport of polar molecules, such as peptides, into the brain. Preliminary data in vivo indicate that the efficacy of COG 133 and other ApoE peptide mimetics can be significantly improved by conjugation to a protein transduction domain (PTD). PTDs are short basic peptides that promote the intracellular delivery of cargo that would otherwise fail to, or only minimally, traverse the cell membrane. However, the ability of a PTD to transport cargo intracellularly does not guarantee it is capable of transport through the BBB, which is significantly more complex of a process, and the number of PTDs tested for the transport of cargo across the BBB in vivo has been relatively few. Therefore, the appropriate PTD for BBB transport needs to be determined empirically, and/or created by modifications of known PTDs.

The present invention also provides methods of using the agents described herein to treat, prevent or ameliorate central nervous system (CNS) injuries and disorders and the like in peripheral tissues such as arthritic joints, lungs and heart. In one embodiment, the present invention also provides methods for reducing neuronal cell death or suppressing macrophage activation. In another embodiment, the present invention provides methods for treating atherosclerosis or reducing atherosclerotic plaques. In yet another embodiment, the present invention provides methods for the treatment, prevention or amelioration of the symptoms of bacterial sepsis.

One aspect of the present invention provides methods for suppressing glial or microglial activation, either in vitro or in a mammalian subject, by administering at least one ApoE analog capable of modulating SET as described above. In one embodiment, the methods provide that the compound can be administered in an amount that reduces glial or microglial activation.

One aspect of the present invention provides methods of treating or ameliorating symptoms associated with CNS trauma, CNS inflammation, cerebral ischemia or cerebral edema by administering at least one agent capable of modulating SET activity. The at least one agent can be administered in an amount that reduces CNS trauma, CNS inflammation, cerebral ischemia or cerebral edema as compared to that which would occur in the absence of the agent. In certain embodiments, the methods of the invention reduce CNS trauma, CNS inflammation, cerebral ischemia or cerebral edema following traumatic brain injury. In certain embodiments, the methods hasten recovery from traumatic brain injury. In certain embodiments, the methods improve functional recovery or cognitive function following traumatic brain injury.

In another aspect of the invention, methods are provided for treating or ameliorating symptoms of inflammation by administering at least one agent capable of modulating SET activity to a subject diagnosed with a disease or disorder associated with inflammation. The at least one agent can be administered in an amount that reduces one or more symptoms, such as pain, associated with the disease as compared to that which would occur in the absence of the agent. In certain embodiments, the methods hasten recovery from a traumatic injury. In certain embodiments, the methods improve symptoms associated with a chronic inflammatory disease such as Crohn's disease.

The methods of the invention can also be used to improve symptoms associated with automimmune inflammatory disease. Some non-limiting examples of autoimmune diseases include rheumatoid arthritis, psoriasis, lupus, multiple sclerosis, colitis, and diabetes (type 1). The inventors have shown in examples below that modulation of SET by a peptide of the invention results in reduced p38MAP kinase phosphorylation, and thus reduced activation. Inhibitors of p38MAP kinase activity have been shown to be important therapeutic compounds for the treatment of rheumatoid arthritis (see review Westra and Limburg (2006) Mini-Reviews in Medicinal Chemistry 6:867-874). Therefore, modulation of SET by ApoE analogs may ameliorate the symptoms associated with rheumatoid arthritis by reducing p38MAP kinase activation. In addition, it has been reported that certain isoforms of p38 MAP kinase as well as extracellular regulated kinase (ERK)1/2 are hyperactive in psoriatic skin lesions (Johansen et al. (2005) British Journal of Dermatology 152: 37-42). Thus, ApoE peptides may be effective in treating psoriasis as well by reducing activation of these two MAP kinase cascades.

In another embodiment, the present invention provides methods of suppressing macrophage activation in a mammalian subject, by administering at least one agent capable of modulating SET. The at least one agent can be administered in an amount that suppresses macrophage activation as compared to activation that would occur in the absence of the compound.

In one embodiment, the present invention provides methods of treating or ameliorating the symptoms of diseases associated with inflammation by the administration of an agent capable of modulating SET. For instance, the present invention provides methods of treating or ameliorating the symptoms of arthritis and rheumatic diseases. In certain embodiments, the methods provide for the treatment or amelioration of the symptoms of rheumatoid arthritis, psoriatic arthritis, ankylosing spondilitis and the like.

In another embodiment, the present invention provides methods of treating or ameliorating the symptoms of multiple sclerosis (MS). In certain embodiments, the methods provide for the treatment or amelioration of the symptoms of relapsing/remitting MS, secondary progressive MS, progressive relapsing MS or primary progressive MS comprising administering at least one compound described herein.

The present invention further provides novel treatments for inflammatory bowel disease (IBD), Crohn's Disease and ulcerative colitis, comprising administering to a subject in need thereof an agent capable of modulating SET. ApoE mimetic peptides such as COG 133 or COG 1410 can be administered to a patient diagnosed with, i.e. suffering from, an inflammatory disease such as inflammatory bowel disease (IBD), Crohn's Disease or ulcerative colitis for reduction of symptoms of said disease compared to that which would occur in the absence of the agent.

In another embodiment, the present invention provides methods of treating atherosclerosis or of reducing the formation of atherosclerotic plaques, comprising administering at least one agent capable of modulating SET as described herein. The at least one agent can be administered in an amount that reduces the formation of atherosclerotic plaques as compared to that which would occur in the absence of the agent. In certain embodiments, the methods provide for the prevention of atherosclerotic plaque development by administering at least one agent as described herein.

In yet another embodiment, the present invention provides methods for the treatment, prevention or amelioration of the symptoms of bacterial sepsis by the administration of at least one agent capable of modulating SET as described herein. The agent(s) can be administered in an amount that reduces sepsis-associated inflammation as compared to that which would occur in the absence of the agent(s).

The present invention also provides a method for the treatment of leukemia, such as chronic myelogenous leukemia (CML) and chronic lymphocyte leukemia (CLL), comprising administering at least one agent capable of modulating SET in an amount that would reduce symptoms of the disease as compared to that which would occur in the absence of the agent. SET is overexpressed in leukemia and inhibits PP2A, thus maintaining activation of the oncogenic BCR/ABL kinase pathway (Neviani et al. (2005) Cancer Cell. 8: 355-368). Therefore, administration of an ApoE mimetic peptide, such as COG 133, COG 1410, or any other ApoE analog, would bind to SET relieving its inhibition of PP2A. PP2A would then be free to dephosphorylate regulators of cell proliferation and survival as well as suppress the oncogenic activity of the BCR/ABL kinase thus reducing leukemogenesis.

PP2A has been reported to negatively regulate endothelial cell motility, which is required for angiogenesis and tumor metastasis in cancers (Gabel et al., 1999, Otolaryngol Head Neck Surg. 121: 463-468; Young, M R., 1997, Adv Exp Med Biol. 407: 311-318) Inhibition of PP2A by okadaic acid increased cell motility by disrupting the cytoskeletal network thereby enhancing the invasive properties of the tumor cells. These results suggest that pharmacologic approaches to activate PP2A would reduce tumor cell metastasis and cancer-associated angiogenesis. Thus, the peptides of the present invention may be useful in treating a wide variety of cancers by increasing the pool of active PP2A within a cell by binding to SET.

In another embodiment, the invention provides a method for the treatment of myelodysplastic syndromes (MDS), a group of diseases in which the production of blood cells by the bone marrow is disrupted. The method comprises administering an amount of at least one agent capable of modulating SET that would result in the reduction of symptoms of MDS compared to that which would occur in the absence of the agent. Symptoms include, but are not limited to, weakness, fatigue, frequent infections, easy bruising, bleeding, fever, and weight loss. p38 MAP kinase has been reported to be constitutively active in MDS and inhibition of p38 MAP kinase activity leads to enhancement of hematopoiesis (Navas et al. (2006) Blood 108: 4170-4177). Since the inventors have shown that modulation of SET by exogenous agents results in decreased p38MAP kinase activity, ApoE mimetic peptides and analogs, which bind to and modulate SET activity, would be useful in treating MDS.

In another embodiment, the present invention provides a method for the treatment of tuberous sclerosis comprising administering an amount of at least one agent capable of modulating SET that would result in the reduction of symptoms of tuber sclerosis compared to that which would occur in the absence of the agent. Tuberous sclerosis is a genetic disorder which causes development of benign hamartomas in many organs, including brain, kidney, heart, skin, and eyes. Serious clinical complications of the harmatomas can result in mental retardation, seizures, and autism, renal dysfunction, dermatological abnormalities, and heart problems. The gene products mutated in this disorder normally function in suppressing ribosomal S6 kinase activity and thus protein synthesis. S6 kinase activity appears to be upregulated in this disorder (see U.S. Pat. No. 7,169,594). Rapamycin, a compound that inhibits protein synthesis, through inhibition of S6 kinase activity has been purported to exert its inhibitory effect through a PP2A-dependent mechanism (see U.S. Pat. No. 7,169,594). Furthermore, S6 kinase activity can be reduced through activation of PP2A (Cho et al. (2006) American Journal of Physiology—Cell Physiology 291: C317-326). Modulation of SET by agents of the present invention can increase PP2A activity (see Example 5). Therefore, agents which inhibit SET and in turn, activate PP2A would reduce aberrant S6 kinase activity associated with tuberous sclerosis and may reduce symptoms of the disease.

One of the characteristic neuropathological features of Alzheimer's disease is the formation of neurofibrillary tangles in the brains of individual's afflicted with the disease. Tau protein, which is a member of the family of microtubule-associated proteins, is one of the major constituents of the fibrillar lesions. In Alzheimer's disease, the neurofibrillary lesions consist of paired helical filaments (PHFs) and straight filaments, both of which are composed of abnormally hyperphoshorylated Tau protein (Goedert et al., 1988, Proc. Natl. Acad. Sci. USA 85: 4051-4055; Kondo et al., 1988, Neuron 1: 827-834; Kosik et al., 1988, Neuron 1: 817-825; Wischik et al., 1988, Proc. Natl. Acad. Sci. USA 85: 4506-4510; and Lee et al., 1991, Science 251: 675-678).

In addition to Alzheimer's disease, other neurodegenerative disorders are characterized by filamentous tau pathology, which appears to lead to neuronal loss in the affected brain regions. These disorders are collectively known as tauopathies and include such diseases as progressive supranuclear palsy (PSP), corticobasal degeneration (CBD), Pick's disease (PiD), argyrophilic grain disease (AGD), and frontotemporal dementia with parkinsonism linked to chromosome 17 (FTDP17). Similar to the neurofibrillary tangles in Alzheimer's disease, the fibrillar lesions in PSP, CBD, and PiD contain hyperphosphorylated tau proteins (Sergeant et al., 1997, FEBS Lett. 412: 578-582; Sergeant et al., 1999, J. Neurochem. 72: 1243-1249; Schmidt et al., 1996, J. Neuropathol. Exp. Neurol. 55: 534-539; Buee-Scherrer et al., 1996, Acta Neuropathol. 91: 351-359; and Probst et al., 1996, Acta Neuropathol. 92: 588-596).

Several kinases and phosphatases have been reported to regulate the phosphorylation state of tau protein. (for review, see Billingsley and Kincaid, 1997, Biochem. J. 323: 577-591 and Buee et al., 2000, Brain Res. Rev. 33: 95-130). One kinase thought to contribute to the aberrant hyperphosphorylation of the tau protein is cyclin-dependent kinase 5 (cdk5). Cdk5 activity is dependent on the activator protein p35. Cleavage of p35 to p25 by the calcium-activated protease calpain leads to constitutive activation of cdk5 activity (for review, see Camins et al., 2006, Drug News and Perspectives 19: 453-460). The truncated p25 protein has been reported to accumulate in the neurons of Alzheimer's disease patients, and p25 accumulation is correlated with increased cdk5 activity (Patrick et al., 1999, Nature, 402: 615-622). Furthermore, expression of the cdk5/p25 complex in several cell lines leads to increased phosphorylation of tau protein and destabilization of the cytoskeletal network. Other studies have shown a correlation between cdk5/p25 activity and hyperphosphorylation of tau protein (for review see Giese et al., Neuroreport 16: 1725-1730 and Kesavapany et al., 2007, Biotechnology Journal 2: 978-987). Cdk5/p25 activity can also phosphorylate neurofilament proteins, which cause pathological lesions in Parkinson's disease and amyotrophic lateral sclerosis (Kesavapany et al., 2007, Biotechnology Journal 2: 978-987). It has been reported that SET binds to the cdk5/p35 complex in cortical neurons, thereby enhancing cdk5/p35 kinase activity (Qu et al., 2002, J. Biol. Chem. 277: 7324-7332). The peptides of the present invention can reduce the binding of SET to the cdk5/p35 complex (Example 8). Thus, modulation of SET by the peptides of the present invention would act to decrease cdk5 kinase activity, and in turn, reduce phosphorylation of tau and neurofilament proteins preventing fibrillary lesions.

Phosphatase activation is another mechanism of regulation of tau phosphorylation. PP2A can dephosphorylate tau and MAP2 in vitro (Yamamoto et al., 1988, J. Neurochem. 50: 1614-1623). The activities of PP2A are believed to be compromised in the Alzheimer's disease brain. Expression of mRNA coding for the catalytic and regulatory subunits of PP2A is decreased in the hippocampus from Alzheimer's patients, suggesting that PP2A activity may be suppressed in the disease (Vogelsberg-Ragaglia et al., 2001, Experimental Neurology 168: 402-412). Suppression of PP2A activity could lead to hyperphosphorylation of tau protein, formation of neurofibrillary tangle formation, and neuronal degeneration. Messenger RNA expression of SET, also known as protein phosphatase 2A inhibitor 2 protein ($I_2^{PP2A}$), is increased in the neocortex of Alzheimer's patients relative to age-matched controls (Tanimukai et al., 2005, Am J. Pathol. 166: 1761-1771). In addition, a shift in the cellular localization of $I_2^{PP2A}$ from the nucleus to the cytoplasm was also observed. Finally, $I_2^{PP2A}$ was co-localized with PP2A and abnormally hyperphosphorylated tau protein in neurons from Alzheimer's patients. Thus, inhibition of PP2A activity by SET contributes to the hyperphosphorylation of tau and the formation of neurofibrillary tangles.

The peptides of the present invention can bind to and modulate SET activity. The inventive peptides have been shown to increase PP2A activity (Example 5) and decrease phosphorylation of tau protein in vivo (Example 7). Thus, the SET modulating agents of the present invention are useful for treating diseases associated with intraneuronal and glial fibrillary lesions, such as Alzheimer's disease and other tauopathies as described above. Administration of agents that modulate SET would have a two-pronged effect. By binding to and inhibiting SET interaction with its target proteins, agents of the invention would decrease cdk5 kinase activity and increase PP2A activity, both of which would lead to a decrease in phosphorylation of tau protein, thereby preventing or lessening the formation of fibrillary lesions.

The present invention also contemplates using the inventive peptides in combination with other SET inhibitors, activators of PP2A, and/or inhibitors of cdk5/p35 activity to achieve an enhanced or synergistic therapeutic effect. For example, the peptides of the invention could be combined with a cdk5/p35 inhibitor to decrease tau phosphorylation. Some non-limiting examples of suitable cdk5 inhibitors include aloisine-A, indirubin-3'-oxime, N4-(6-aminopyrimidin-4-yl)-sulfanilamide, 3-amino-1H-pyrazolo[3,4-b]quinoxaline, butyrolactone I, aminopurvalanol A, alsterpaullone, and roscovitine. Additional suitable inhibitors of SET and cdk5/p35 activity and activators of PP2A encompass peptides, small molecules, antibodies and fragments thereof, and nucleic acids including, but not limited to, antisense, siRNA, shRNA, miRNA, and aptamers.

In certain embodiments, the invention provides pharmaceutical compositions comprising at least one agent capable of modulating SET. In certain embodiments, the invention provides pharmaceutical compositions comprising at least one agent capable of modulating SET with another drug for the treatment, prevention or amelioration of an inflammatory disease or condition such as CNS or neurologic injury, rheumatic diseases, multiple sclerosis, CABG surgery, atherosclerosis or bacterial sepsis. The pharmaceutical compositions of the agents of the present invention can be provided in such a way as to facilitate administration to a subject in need thereof, including, for example, by intravenous, intramuscular, subcutaneous or transdermal administration. See, Remingtons Pharmaceutical Sciences, 19th ed. Remington and Gennaro, eds. Mack Publishing Co., Easton, Pa., incorporated herein by reference. The methods of the present invention further provide for various dosing schedules, administration times, intervals and duration to treat, prevent or ameliorate the disorders described herein. Also included are functional variants of the disclosed agents and variants identified using the assays disclosed in the present invention and known in the art, wherein such agents are capable of modulating SET. Consistent therewith, the invention also includes use of the disclosed agents and functional variants thereof in methods of making medicaments for treating the various diseases and disorders discussed herein.

In one embodiment of the present invention, agents can be identified that are capable of binding to SET and modulating SET activity. Agents can be screened for the ability to bind to SET by methods known in the art. For instance, agents can be identified by screening libraries using methods such as phage display, yeast display, or a ligand displacement assay. Agents capable of binding to SET can further be screened for their ability to compete with or inhibit the binding of a peptide containing COG 133 (SEQ ID NO: 1). Agents capable of competing with or inhibiting the binding of a peptide containing COG 133 may be more effective than COG 133 at modulating SET activity. For instance, agents such as COG 1410 which are more effective than COG 133 as described above and in the examples below, is capable of competing with COG 133 for binding to SET.

Figure 4:
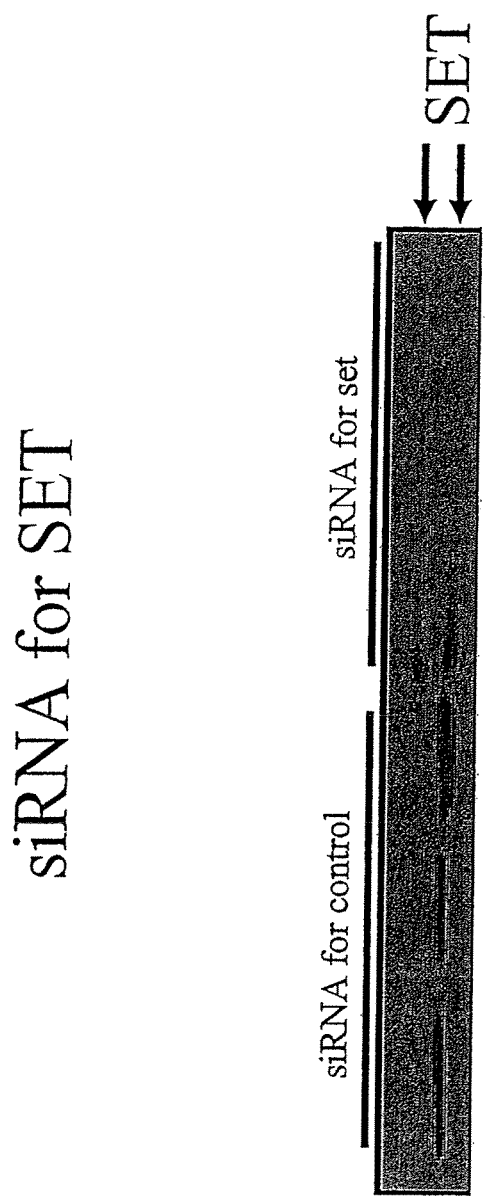
FIG. 4 is a gel image indicating the amount of SET produced in the presence of SET siRNA.

Agents found to bind to SET can be isolated and further tested for their ability to modulate PP2A activity or cdk5 activity. Methods of measuring phosphatase and kinase activity are known in the art and include, but are not limited to, in vitro phosphorylation assays that monitor release or incorporation of phosphate into a peptide substrate, and western blot methods detecting phosphorylation status of endogenous substrates in cellular lysates.

Screening methods provided in the present invention can be used to screen for agents capable of modulating SET for the treatment of neurological, inflammatory, and proliferative diseases including, but not limited to, multiple sclerosis, vasculitis, acute disseminated encephalomyelitis, Guillain-Barre syndrome or sepsis, acute CNS injury such as traumatic brain injury, stroke, closed head injury, global cerebral ischemia, cerebral edema, focal ischemia or intracranial hemorrhage, or a chronic neurological disease such as Alzheimer's disease, tauopathies, HIV-associated encephalopathy, neurolathyrism, amyotrophic lateral sclerosis (ALS), Huntington's chorea, Parkinson's disease, epilepsy, d-2-hydroxyglutaric aciduria, schizophrenia, leukemia, myelodysplastic syndrome (MDS), or tuberous sclerosis.

The examples which follow are set forth to illustrate the present invention, and are not to be construed as limiting thereof.

Example 1: Identification of SET

COG 133-biotin or a biotin control was added to total protein from BV2 microglial cells. Proteins binding to Cog-biotin or biotin were collected by immunoprecipitation with streptavidin beads. Beads were extensively washed to remove non-specifically bound proteins. Proteins specifically bound to the streptavidin were eluted and denatured with laemmli sample buffer and run on an SDS/PAGE gel. After electrophoresis, the gel was stained by coomassie/silver stain to visualize protein bands.

FIG. 1 provides a silver stained image of the SDS/PAGE gel and results of the experiment. The COG-biotin lanes labeled A and B contain two bands not present in the biotin control lane of the gel. Silver stained bands containing the COG 133-binding protein were excised from the gel, and protein was extracted from the gel slices, digested with a protease like trypsin, and the proteolytic fragments analyzed by mass spectrometry. The sequence of selected proteolytic fragments was accomplished by the MS/MS method. The sequences of the proteolytic fragments and their molecular weights were compared against amino acid sequences and molecular weights of known sequences in the NCBI GenBank by methods known in the art. Analysis showed that the two bands on the gel correspond to known variants of SET (SEQ ID NOs: 3 and 4).

Example 2: COG-Biotin Interacts with SET Protein Directly

BV2 microglial cells were cultured and contacted with biotin labeled COG 133. Total protein extracts were prepared from treated BV2 cells and biotin-containing complexes isolated with streptavidin-agarose beads. After washing of beads, proteins were eluted by boiling in Laemmli sample buffer and denatured proteins were separated on a SDS-PAGE gel. Proteins separated by SDS-PAGE were transferred to nitrocellulose, and Western blots probed with anti-SET antibodies. Blots were washed to remove non-specifically bound primary antibodies. The blots were then incubated for 1 hour with goat-anti-rabbit/horse radish peroxidase-coupled secondary antibodies followed by washing and development with a chemiluminescent HRP-antibody detection kit (Denville Scientific). Blots were exposed to x-ray film for various lengths of time. Immunoreactive bands were visualized as dark bands on the film.

FIG. 2 provides a blot image and legend. The first lane of the blot corresponds to a biotin control. Lane two corresponds to biotinylated COG 133 from total protein. The two protein bands that uniquely bind to biotin-COG 133 correlate to two splice variants of SET. Lane three corresponds to biotinylated COG 133 and 20×COG 133. Lane four of the blot corresponds to biotinylated COG 133 and pep96. Pep96 has no biological activity but is structurally similar to COG. Lane five corresponds to biotinylated COG 133 and COG 1410. COG 1410 is a more potent variant of COG 133. The faint bands correlating to SET indicate that COG 1410 competes with COG 133 in binding to SET.

Example 3: Nitrite/MTT in BV2 Cells Treated with siRNA for SET

COG 133 has previously been shown to reduce LPS-induced nitric oxide production (Lynch et al. 2005). See PCT application PCT/US05/31431 which claims priority to U.S. Provisional Applications 60/606,506, filed Sep. 2, 2004, 60/608,148, filed Sep. 9, 2004, and 60/606,507, filed Sep. 2, 2004 which are herein incorporated by reference in their entireties. BV2 cells were transfected with siRNA to SET. BV2 cells transfected with the siRNA and BV2 cells not transfected with the siRNA were treated with COG 133, LPS, or LPS and COG 133 as described in the above-referenced patent applications. Untreated BV2 cells were used as a control. FIG. 3 is a graph of the results. Bars three and seven correspond to LPS without siRNA to SET and with siRNA to SET, respectively. Bar seven shows a significant reduction in nitric oxide compared to bar 3, thus demonstrating that LPS-induced nitric oxide production is reduced when the amount of SET is reduced. Similarly, there is a reduction in nitric oxide in the group treated with LPS and COG 133 and transfected with siRNA to SET compared to the group treated with LPS and COG 133 and not transfected with siRNA (lanes 8 and 4, respectively). However, there is not a significant difference in the amount of nitric oxide between lanes 7 and 8 (LPS+siRNA and LPS+COG 133+siRNA, respectively), demonstrating that removal of SET blocks the effects of COG 133 on LPS-induced NO.

FIG. 4 is a gel image of a negative and positive control. The gel image shows that siRNA to SET was able to effectively silence SET.

Figure 5:
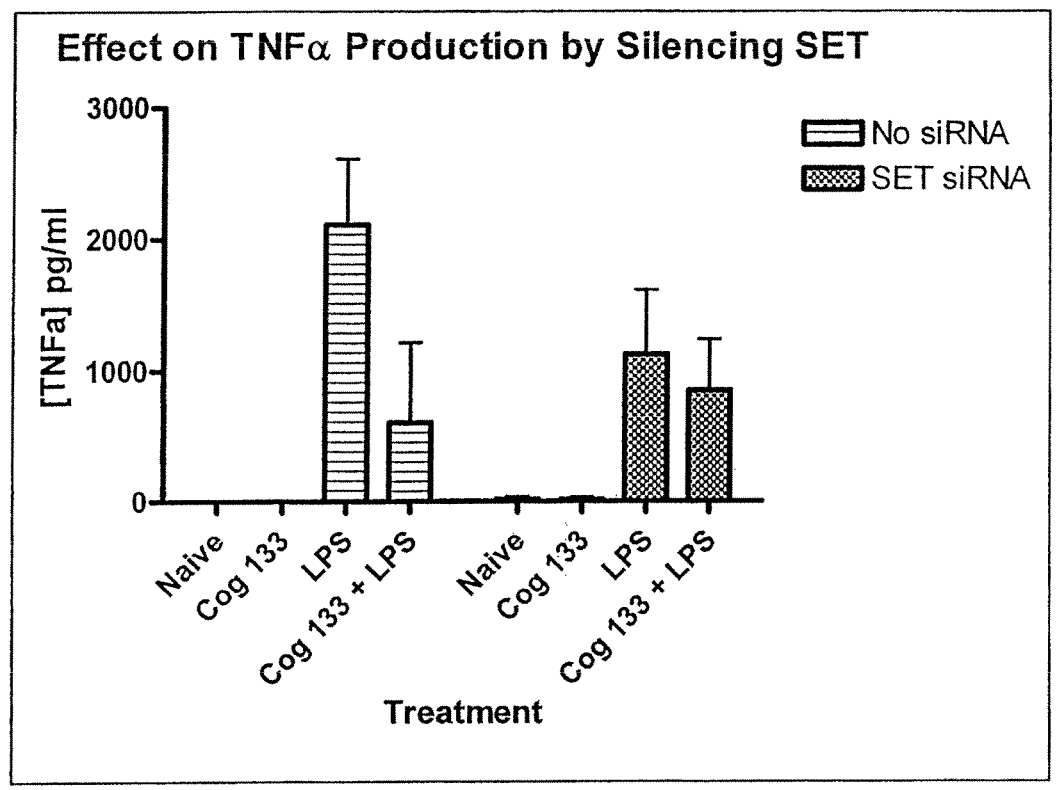
FIG. 5 is a graph showing the amount of TNFα produced in human THP1 cells treated with COG 133, LPS, and LPS+COG 133, both with and without siRNA to SET.

FIG. 5 is a graph of results from a similar experiment in human THP1 cells demonstrating that when SET is removed by siRNA-based silencing, the effect of COG 133 in reducing LPS-induced TNFα production is eliminated. Consistent with the mechanism of SET as an inhibitor of Protein Phosphatase 2A (PP2A), a reduction of the LPS-induced TNF response as well as elimination of the effect of COG 133 was observed when SET was removed from the cells.

Example 4: COG Peptides Compete for Binding to SET from Human Brain

Figure 6:
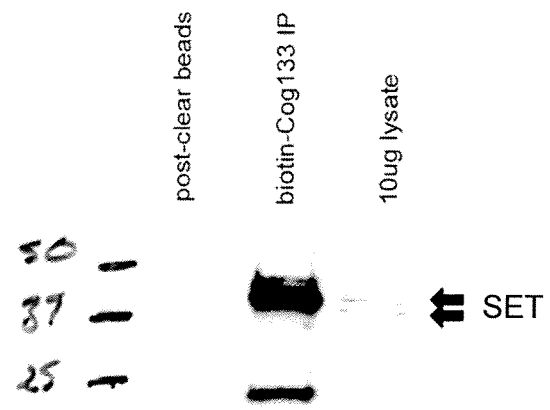
FIG. 6 is a western blot of the human brain SET protein isolated by binding to biotinylated-COG 133.

Human brain was homogenized in PBS buffer with a protease cocktail tablet and centrifuged to remove cellular debris. 100 ng of biotinylated COG 133 (COG 133 peptide with biotin attached to the N-terminus) was added to 1 mg of clarified supernatant. After 4 hours of incubation at room temperature, 50 μL of a 50% slurry of streptavidin agarose beads were added. After an additional hour of incubation, the beads were pelleted by centrifugation. The beads were washed 3 times with PBS buffer containing 0.1% tween 20 detergent. 50 μL of a 2×SDS PAGE loading buffer (containing DTT) were added to the washed beads and the samples were boiled for 2 minutes. Polyacrylamide gels were loaded with either 40 μL of extract per lane or 10 μg of total brain extract protein (control lane) and run in SDS buffer. Proteins were transferred from the gel onto nitrocellulose membranes, which were subsequently blocked with 10% nonfat dry milk. Membranes were then probed with an anti-SET antibody. Blots were developed with Enhanced Chemiluminescence substrates (GE healthcare) and visualized by exposure to film. The blot shown in FIG. 6 demonstrates that biotinylated COG 133 binds to and pulls down SET from human brain extracts.

Figure 7:
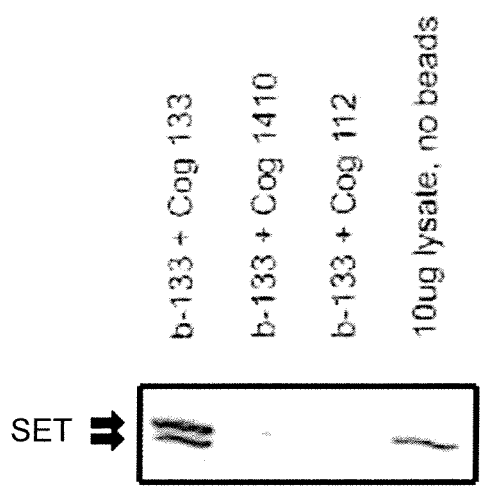
FIG. 7 is a western blot showing that binding of biotinylated-COG 133 to human brain SET protein is blocked by COG 1410 or COG 112.

In a related experiment, derivatives of the COG 133 peptide were tested for SET binding. Human brain extracts were prepared as described above. A 10-fold excess of COG 1410 or COG 112 peptide was added to the brain extract and incubated for 10 minutes. Next, 100 ng of biotinylated COG 133 was added to the extract and incubated for four hours at room temperature. Streptavidin agarose beads were added to the mixture and processed as described above. The samples were prepared for SDS-PAGE and western blot analysis. The blot probed for SET protein (FIG. 7) shows that an excess of either COG 1410 or COG 112 peptide reduces the amount of SET protein pulled down with biotinylated COG 133. These results suggest that these two COG 133 derivatives compete with COG 133 for binding of SET.

Example 5: COG 112 Activates PP2A

Figure 8:
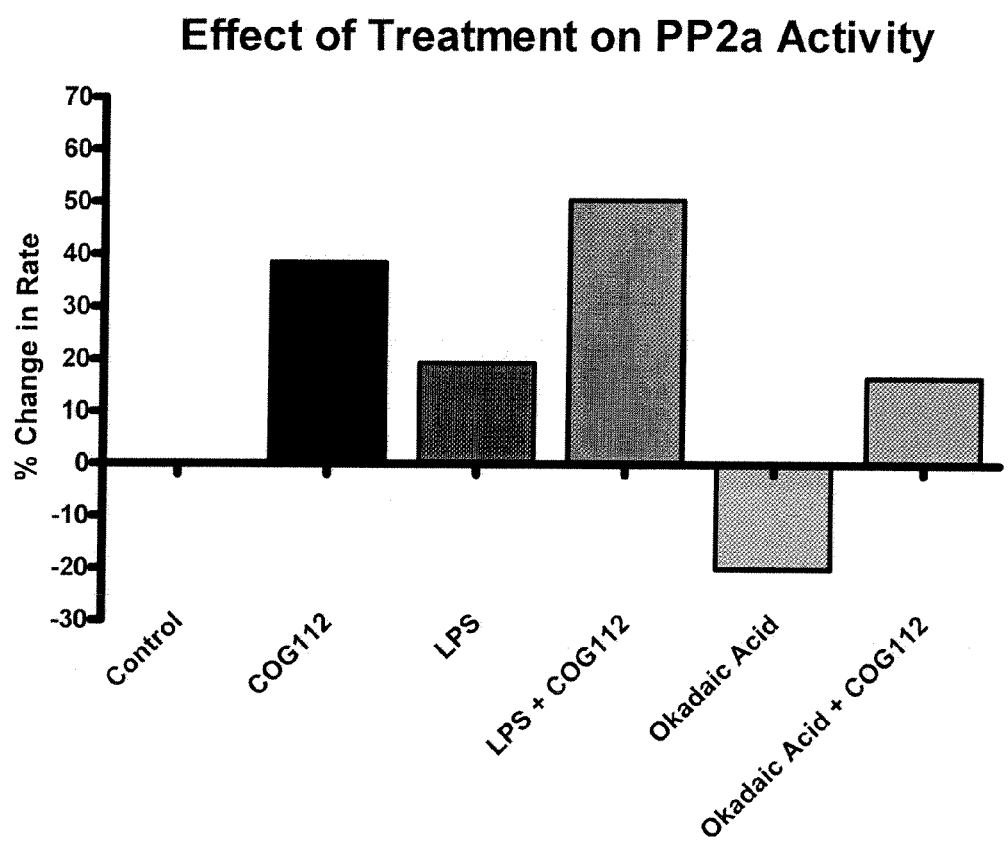
FIG. 8 is a graph of the enzymatic activity of PP2A in cells treated with COG112.

Mouse macrophagic RAW cells were incubated with either 100 ng/mL LPS, 1 μM COG 112 (COG 133 conjugated to antennapedia), LPS and COG 112, 10 nM okadaic acid (an inhibitor of PP2A), or okadaic acid and COG 112. After 1 hour, cells were lysed and PP2A was immunoprecipitated by adding an antibody targeted to the catalytic C-subunit of PP2A. Half of the immunoprecipitate was separated by SDS-PAGE, blotted on to nitrocellulose, and probed with an anti-PP2AC antibody. The remaining portion was assayed for activity by adding 125 μL assay cocktail containing a phospho-threonine substrate peptide to the immunoprecipitated enzyme. After incubating at 37° C. with shaking, a 25 μL aliquot was removed and added to an ammonium molybdate solution (Upstate) that chelates free phosphate and changes color upon chelate formation. Aliquots were removed at various time intervals and the amount of free phosphate released from the peptide was determined by comparison to a phosphate standard curve. The rate of phosphate release was determined by linear fit to the time course data and was normalized to the relative PP2A concentration. PP2A activity, measured by the rate of phosphate release, is increased in the presence of COG 112 (FIG. 8), as would be expected if SET inhibition of PP2A was eliminated by binding of COG112 to SET. This result suggests that an equilibrium exists between active PP2A and inactive PP2A bound to SET and this equilibrium can be shifted to modulate the amount of active PP2A enzyme. To test this hypothesis, macrophage cells were incubated with okadaic acid alone or in the presence of COG 112. The pool of PP2A not bound to SET would be inhibited by okadaic acid, thus producing a decrease in baseline PP2A activity (FIG. 8). According to the above hypothesis, one would expect that treatment of the cells with COG 112 would increase the pool of active PP2A by binding to SET and releasing the phosphatase from SET inhibition thereby producing an overall increase in PP2A activity. The results shown in FIG. 8 demonstrate that COG 112 does, in fact, increase PP2A activity in the presence of okadaic acid. Thus, the active pool of PP2A in a cell can be regulated by modulating SET activity with ApoE peptides.

Example 6: COG 133 Suppresses Activation of p38 MAP Kinase, JNK, ERK 1/2, and NFκB Mouse BV2 microglia were incubated with either a negative control, LPS, or LPS and COG 133 (SEQ ID NO: 1) peptide for 30 minutes. Cells were lysed and a clarified extract prepared by centrifugation. Polyacrylamide gels were loaded with 30 μg of extract per lane and run in SDS buffer. Proteins were transferred from the gel onto nitrocellulose membranes, which were subsequently blocked with 10% nonfat dry milk. Membranes were then probed with phospho-specific p38 MAP kinase, MKK 3/6, JNK, ERK, and IκB antibodies. Membranes were developed with Enhanced Chemiluminescence substrates (GE healthcare) and visualized by exposure to film. Membranes were then stripped and reprobed for total p38, JNK, Erk or IκB using non phospho-specific antibodies as previously described. A representative western blot depicting the phosphorylation of p38 MAP kinase is shown in FIG. 9A. In some experiments, the membranes were probed for GAPDH protein. Densitometry analysis of the western blots was conducted and the signals from phosphorylated p38 MAP kinase were normalized to those from GAPDH. The densitometry analysis is shown in FIG. 9B. These results indicate that treatment with COG 133 causes a decrease in phosphorylation and thus deactivation of p38 MAP kinase. PP2A has been reported to bind and dephosphorylate p38 MAP kinase (Sundaresan & Farndale 2002 FEBS Letters 528, 139). Given that COG peptides can increase PP2A activity (Example 5), it is likely that the dephosphorylation of p38 MAP kinase occurs through the activation of PP2A by COG binding to SET.

Figure 10:
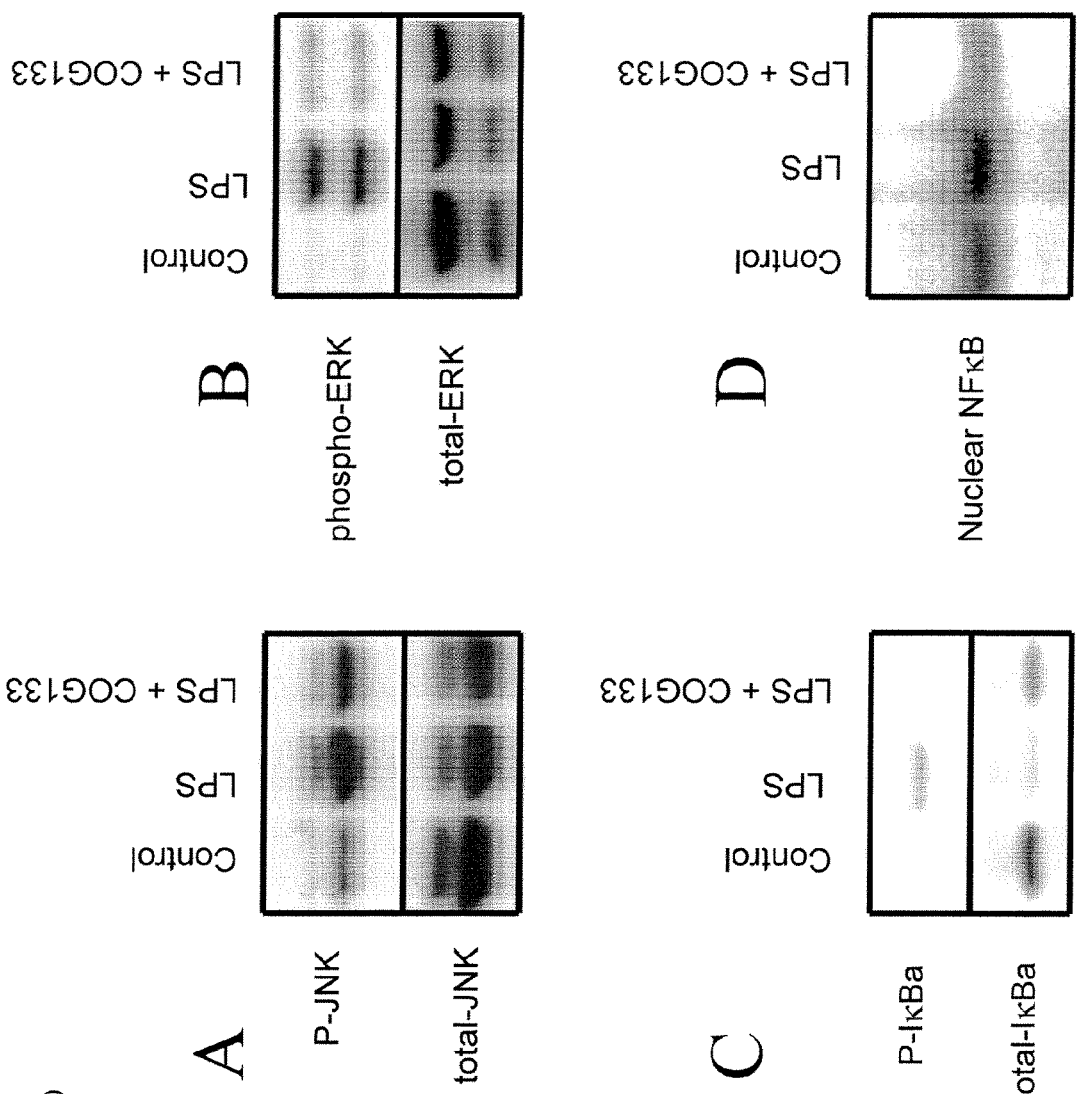
FIG. 10 shows the suppression of LPS-induced phosphorylation of c-Jun N-terminal kinase (JNK) (A), extracellular regulated kinase (ERK) 1/2 (B), and IκBa (C) by COG 133. Panel D depicts a reduction in nuclear NFκB in cells treated with COG 133.

FIG. 10 shows representative western blots from the experiments described above for phospho JNK (panel A), ERK (panel B), and IκB (panel C). The results of these experiments show that the COG 133 peptide reduces the LPS-induced phosphorylation of these signaling proteins demonstrating that COG 133 suppresses the activation of these signaling cascades, presumably through the inhibition of SET and the subsequent activation of PP2A.

In the dephosphorylated state, IκB binds to the transcription factor NFκB and prevents it from translocating to the nucleus to activate transcription of pro-inflammatory cytokines. To determine if COG 133 also reduced the translocation of NFκB to the nucleus, colonic epithelial cells were stimulated with LPS alone or in the presence of COG 133 and nuclear extracts were prepared from the stimulated cells. A radiolabeled oligonucleotide containing a NFκB binding site was added to the proteins from the nuclear extracts and the proteins were subsequently separated by non-denaturing polyacrylamide gel electrophoresis. The amount of NFκB present in the nuclear extracts was detected by autoradiography (FIG. 10D). Nuclear NFκB was reduced in the presence of COG 133 providing further evidence that this signal transduction cascade is suppressed in cells treated with ApoE peptides.

Example 7: COG 1410 Reduces Tau Phosphorylation

C57B1/6 mice were injected intravenously with increasing concentrations of okadaic acid (OA) (calculated by administration of a sufficient quantity of OA to produce the indicated µM concentration in a blood volume of 2 mL). One hour after OA was administered, mice were euthanized by decapitation and the brain removed. The cortex was isolated, flash frozen with liquid nitrogen, ground to a fine powder and an extract made by homogenization of the powder in an extraction buffer containing protease and phosphatase inhibitors. Protein extracts were separated by SDS-PAGE, transferred to nitrocellulose membranes, and probed for phospho-tau using the AT-8 antibody that recognizes phosphorylation of Ser202 and Thr205 of tau. Phospho-tau signals were normalized to signals from GAPDH protein. The results of this experiment show that inhibition of PP2A by OA produced a concentration-dependent increase in phospho-tau in the cortex (FIG. 11A), indicating that PP2A regulates the phosphorylation status of the tau protein in vivo. To determine the effect of COG peptides on the phosphorylation status of the tau protein, 5 mg/kg of COG 1410 was administered to the mice by subcutaneous injection 15 minutes prior to OA administration. FIG. 11B depicts the results of this series of experiments. COG 1410 reduced the amount of phosphorylated tau protein induced by OA. It is likely that the effect of COG 1410 on phospho-tau is mediated through COG 1410 binding to SET protein, thereby activating PP2A.

Example 8: COG Peptides Reduce the Interaction of SET with p35

Figure 12:
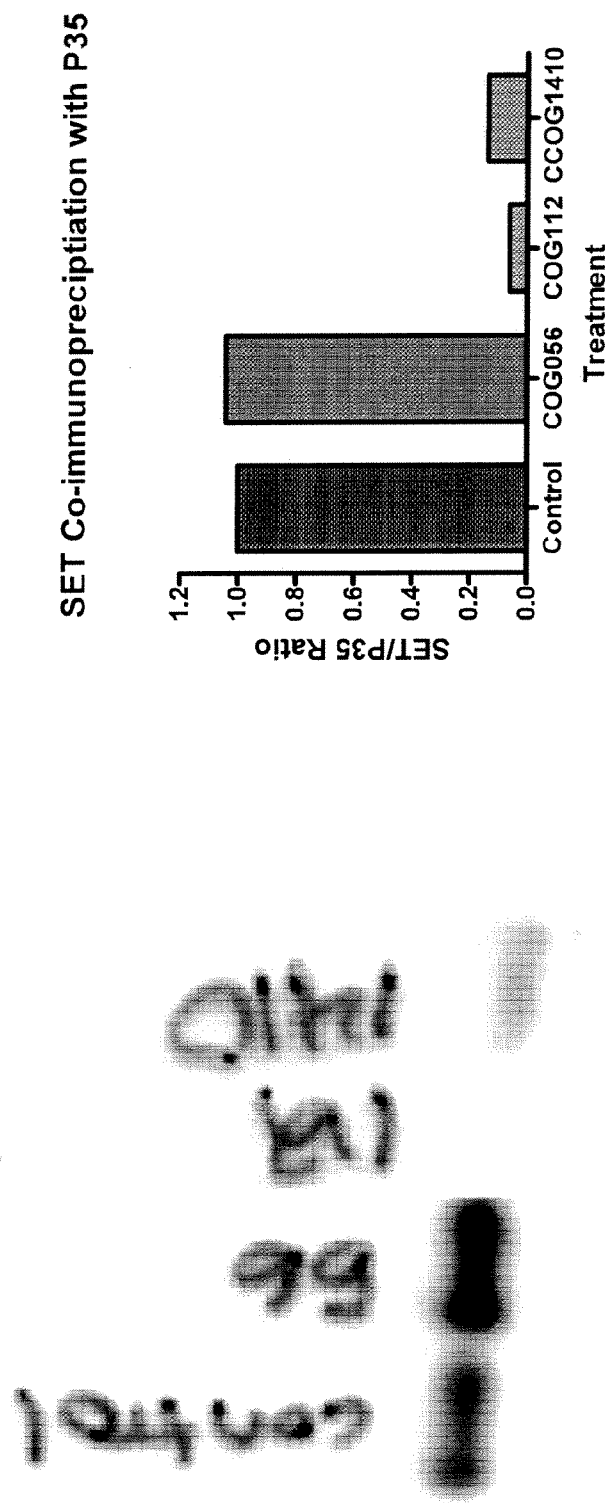
FIG. 12. Mouse brain lysate was incubated with 50 μM of each of the peptides indicated. P35 was subsequently immunoprecipitated from 1 mg of the peptide-treated lysate. Western blots were performed to measure co-precipitation of SET protein (left panel). Densitometry analysis (right panel) shows that COG 112 and COG 1410 reduce the amount of SET bound to P35. COG 056, which is the reverse sequence of COG 133 and has no biological activity, has no effect on SET binding to P35. Signals from SET were normalized to signals for P35 protein. Results with COG 133 are not shown and were inconclusive possibly due to unequal protein loading.
Figure 13:
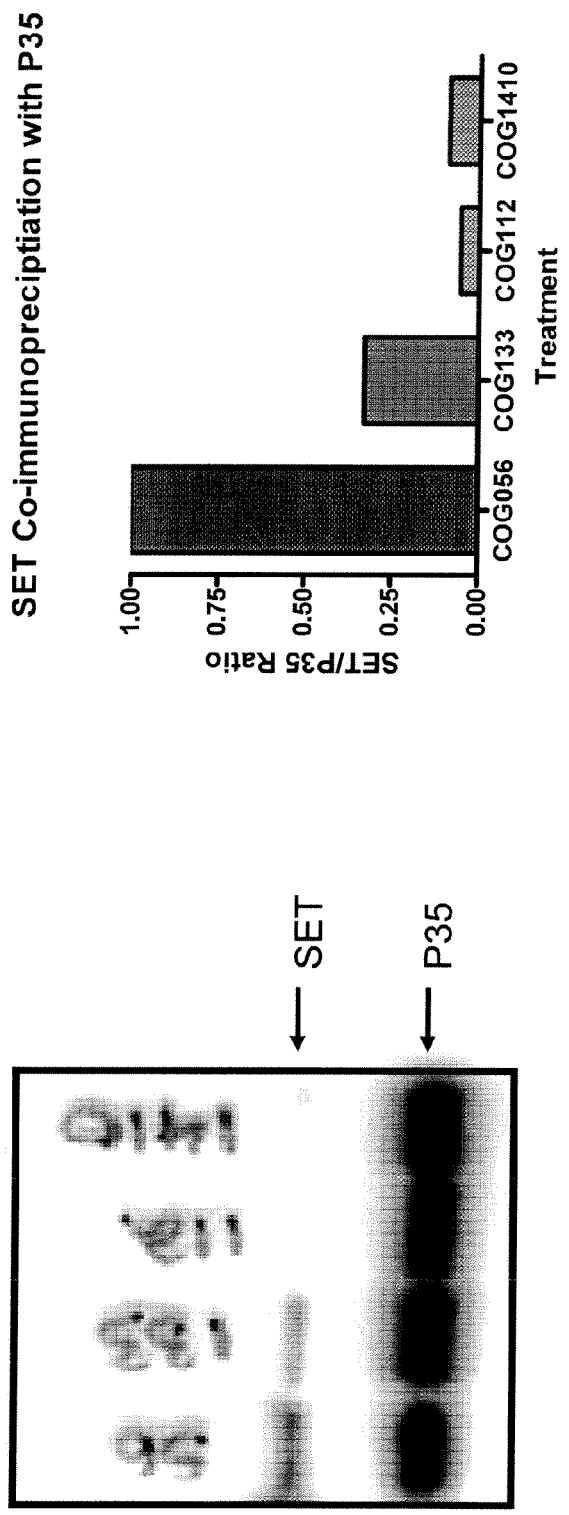
FIG. 13. Human brain lysate was incubated with 50 μM of each of the peptides indicated. P35 was subsequently immunoprecipitated from 1 mg of the peptide-treated lysate. Western blots were performed to measure co-precipitation of SET protein (left panel). Densitometry analysis (right panel) shows that COG133, COG 112, and COG 1410 reduce the amount of SET bound to P35. COG 056, which is the reverse sequence of COG 133 and has no biological activity, has no effect on SET binding to P35. Signals from SET were normalized to signals for P35 protein.

Cdk5 requires the activator protein p35 for kinase activity. Although cdk5 is ubiquitously expressed, p35 expression is restricted to neurons of the central nervous system, thus limiting cdk5 associated kinase activity to these neurons. Cleavage of p35 to p25 disregulates cdk5 kinase activity causing the kinase to become constitutively active. Constitutive kinase activity of cdk5/p25 has been implicated in the aberrant hyperphosphorylation of tau protein and subsequent neurodegeneration found in Alzheimer's disease and other tauopathies. SET protein has been shown to bind to cdk5/p35 complexes and enhance kinase activity (Qu et al., 2002, J. Biol. Chem. 277: 7324-7332). Therefore, it may be possible to reduce cdk5 kinase activity by interfering with the interaction between SET and the cdk5/p35 complex. To test this possibility, the effects of COG peptides on the binding of SET to p35 were examined. Mouse brain lysates (FIG. 12) or human brain lysates (FIG. 13) were incubated with 50 µM of COG 056 (reverse sequence of COG133), COG 112, COG133, or COG 1410. Activator protein p35 was immunoprecipitated with an anti-p35 antibody and protein A agarose beads from 1 mg of the peptide-treated brain lysates. P35 immunoprecipitated protein was separated by SDS-PAGE, transferred to nitrocellulose, and probed with an antibody to SET and P35. Signals from SET were normalized to those from P35 to control for minor differences in protein loading. The results from experiments from mouse brain lysate are shown in FIG. 12 while the results from experiments from human brain lysate are shown in FIG. 13. The densitometry analysis demonstrates that while COG 056, which is inactive in biological assays, does not reduce the amount of SET bound to P35, COG 112, COG 1410, and COG 133 effectively inhibit the binding of SET to P35.

Cellular lysates from cells treated with COG peptides can be assayed for cdk5 activity using an in vitro phosphorylation assay with a histone peptide as a substrate as previously described (Qi et al., 1995, J. Biol. Chem. 270: 10847-10854). It would be expected that cells treated with COG 112, COG 133, or COG 1410 would exhibit less cdk5 activity than untreated cells or cells treated with COG 056. These results would suggest that SET is an in vivo regulator of cdk5 activity in neurons and this regulation can be modulated by COG peptides.

Example 9: Isolation of SET Binding Agents by Phage Display

Phage display was first described in 1985 and is based on a physical linkage between phenotype, a peptide displayed on the surface of a phage particle, and genotype, the DNA that encodes the peptide. In his pioneering work, George Smith inserted DNA fragments into gene III of a filamentous bacteriophage and showed that polypeptides encoded by the DNA fragments were displayed as fusions to the pIII coat protein on the surface of the bacteriophage.[1] These "fusion phage" could be selected over ordinary phage using affinity purification with an antibody directed against the recombinant polypeptide. After this initial demonstration of the phage display technology, random peptide libraries were generated in phage display systems and used to epitope map antibodies and to identify mimetic peptides.[2] Phage display of peptide libraries has since proven to be a powerful tool to isolate peptides that can be used for affinity chromatography, to study protein-protein interactions, as surrogate ligands for drug discovery, and to identify peptides that are directed to organs or tissues.[3-12] This has also been extended to create polypeptide materials that possess unique gelation properties, are precursors of liquid crystals, and that mimic the extracellular matrix.[13-16]

In the affinity selection process that is used to isolate these peptides, typically, the target is immobilized on the surface of a microtiter plate and an aliquot of a phage library is added. Following an incubation step to allow for binding by phage that display peptides with an affinity for the target, the plate is washed to remove unbound phage particles. The bound phage are then eluted by treatments that result in denaturation of the target without hindering the viability of the phage. The eluted phage are then added to a bacterial culture and amplified.[17] One round of this affinity selection cycle results in an enrichment of phage that display peptides that bind to the target. Complete enrichment is accomplished by repeating this process for several cycles before plating on a lawn of bacteria to isolate individual phage plaques. The phage in each of these plaques are homogeneous and express a single peptide on their surfaces. The homogeneous phage are tested for binding to the target using an ELISA assay and the peptide sequence of the homogeneous phage population is determined by sequencing the inserted DNA.

Originally, phage display was developed with peptides fused to the amino terminus of the phage coat protein pIII. This results in a peptide fused to each of the 3-5 copies of pIII present on the phage particle and provides peptides that range from picomolar to low micromolar affinity.[1] Lower affinity peptides can be obtained using short peptides (<10 amino acids) displayed at the N-terminus of the major coat protein pVIII.[18] This produces approximately 2700 copies of the peptide per phage particle and this large number of displayed peptides allows for the isolation of peptides with high micromolar affinity. The utility of pIII and pVIII systems has been extended by the development of C-terminal display systems for each phage coat protein. Fuh et. al. described the addition of a linker to the carboxyl terminus of pVIII thereby allowing the display of peptides fused to the end of the pVIII protein. This C-terminal pVIII phagemid system was successfully used to identify peptides that interact with PDZ domains.[19] Modification of the pIII protein has also allowed for the display of polypeptides fused to the C-terminus of pIII.[20]

Phage Display Libraries

The ability to identify high affinity peptides that bind to a target using phage display is highly dependent on the presentation of the peptides on the phage surface and the design of the peptide library that is used for the affinity selection process. Completely random 7 or 12 amino acid libraries and a $CX_7C$ disulfide linked library are commercially available from New England BioLabs. The success rate for identifying binding peptides from these libraries is approximately 20% while success rates that approach 90% can be obtained using libraries with added design features and screening several phage libraries against each target. For example, phage libraries may be generated with the following designs: $X_{11}$, $X_6FX_6$ where F is any fixed amino acid, $CX_{11}$, and $CX_{16}$ using the New England BioLabs PhD M13KE gIII vector system. All libraries are constructed as degenerate oligonucleotides with degenerate codons encoded as NNK, where N=A, C, G, or T and K=G or T. Restriction of the wobble position of the codon improves, but does not eliminate, the codon bias intrinsic to the genetic code where six codons each code for serine, arginine, and leucine, only one codon codes for methionine and tryptophan. The NNK construction also eliminates two of the three stop codons. The complexity of each library will be measured at the time of construction and libraries can be routinely constructed with complexities of $10^8$ to $10^9$ unique sequences. Typical affinity selection experiments are conducted with $1\times10^{11}$ phage such that an average of 100-1000 copies of each peptide in the library are used for each experiment.

Protein Production

Protein for the phage display experiments is prepared from tissue homogenates, cultured cells or by recombinant expression by reported methods. Alternatively, recombinant SET is expressed with an attached biotinylation sequence, known as and AviTag™ (Avidity Systems), fused to the N- or C-terminus of SET. In this case, recombinant expression is performed in bacterial cells that overexpress biotin ligase so that the resulting SET is biotinylated during expression. The biotinylated SET is immobilized at saturating concentrations on streptavidin-coated BSA blocked microtiter plates, typically 20-80 pmol/well, for phage selection.

The SET protein is analyzed before affinity selection by SDS-PAGE for purity and activity in inhibition of PP2a to ensure that the biochemical activity is intact. For biotinylated SET, activity assays are conducted before and after biotinylation. Biotinylated SET is captured on streptavidin-coated 96-well plates and the amount of the SET added to each well is determined by performing a titration of the SET protein in the microtiter plate. After washing the plate to remove unbound SET an excess amount of chemically biotinylated alkaline phosphatase is added to each well. When SET is present at subsaturating concentrations, the alkaline phosphatase binds to the available biotin binding sites on the plate and detection of alkaline phosphatase activity is used to determine the saturation point for the biotinylated SET. For the affinity selection process, excess biotin-binding sites are blocked with biotin prior to the addition of the phage libraries.

Phage Affinity Selection

Affinity selection of peptides is conducted essentially as described by Hyde-deRuyscher et al.[21] Affinity selections are performed by adding one of the previously described phage display libraries to each well of a streptavidin coated, BSA-blocked polystyrene microtiter plate that does not contain immobilized SET. Incubation in this plate allows the polystyrene, streptavidin, and BSA binding peptides to be removed from the phage stock when the phage solution is transferred to the plate containing immobilized SET protein. This preclearing step reduces background binding. The background can be reduced further by alternating the blocking agent at each round of the selection process. Non-fat dry milk and BSA are used as blocking agents with BSA being used in odd numbered selection rounds and milk being used in even numbered selection rounds. After incubation of the phage with SET, the plates are washed to remove unbound phage and to select for phage with a high affinity. To select for high affinity phage, multiple wash steps are performed and the plates are incubated in the wash buffer for several minutes between each wash step. Performing the washing in this way allows for recovery of phage with a very slow release rate ($k_{off}$) to remain bound.

Following plate washing, the bound phage are either eluted as described by Sparks et al.[22] or amplified by direct infection by addition of a culture of E. coli cells to the well and incubation at 37° C. This direct infection method may prove to be superior to phage elution methods for obtaining peptides with high binding affinities. Selected phage are amplified and tested for binding to the desired targets and to controls after each round of affinity selection using standard ELISA assays with an anti-M13 antibody as described below. After three or four rounds of selection phage from positive libraries are plated and individual plaques are amplified and tested to identify individual phage that bind to SET. Phage that bind to SET are tested for specificity by evaluating binding to SET and several unrelated proteins in ELISA assays. The DNA of the amplified individual binding phage is isolated and sequenced to determine the sequence of the peptide responsible for binding to SET.

Phage ELISA Assays

Following affinity selection, eluted phage are amplified in 2×YT and direct infected phage are amplified in situ overnight. The amplified phage are tested in phage ELISAs as described previously.[22] In brief, SET and control proteins are immobilized in microtiter wells, phage are added and allowed to bind, the plates were washed and a horse radish peroxidase (HRP)-linked antibody directed against the major coat protein of the phage is used to detect phage bound to the SET. HRP may be detected using 2,2'-azinobis (3-ethylbenzthazolinesulfonic acid) (ABTS) or TMB as substrate and reading the absorbance in a plate reader. Phage producing a strong signal that is dependent on the presence of SET are plaque purified, amplified and tested for binding to target protein and a series of unrelated proteins in a phage ELISA to verify specificity of binding. Sequencing of phage-displayed peptides is accomplished by preparing single-strand DNA using the Qiagen M13 single-strand prep kit. Automated DNA sequencing is conducted by the Sequencing Facility at Duke University.

Phage Affinity Titrations

The relative affinities of selected phage are determined by conducting phage ELISAs using serial dilutions of phage on a single target protein concentration. An 11-point, twofold dilution series from 50 µL will be used in the titrations. Background signals of SET exposed to antibody but no phage are subtracted from each value. Phage titers are determined by dilution, plating and counting individual plaques and the absorbance readings from the phage ELISAs are plotted as a function of plaque forming units per assay.

LITERATURE CITED

1. Smith, G. P. (1985) Filamentous fusion phage: novel expression vectors that display cloned antigens on the virion surface, *Science* 228, 1315-1317
2. Smith, G. P., and Petrenko, V. A. (1997) Phage display, *Chem. Rev.* 97, 391-410
3. Cwirla, S. E. et al. (1990) Peptides on phage: a vast library of peptides for identifying ligands, *Proc. Natl. Acad. Sci., USA* 87, 6378-6382
4. Devlin, J. J. et al. (1990) Random peptide libraries: a source of specific protein binding molecules, *Science* 249, 404-406
5. Scott, J. K. and Smith, G. P. (1990) Searching for peptide ligands with an epitope library, *Science* 249, 386-390
6. Christensen D J, Gottlin E B, Benson R E, Hamilton P T. (2001) Phage display for target-based antibacterial drug discovery, Drug Discov. Today. 1, 721-727.
7. Ehrlich, G. K. and Bailon, P. (1998) Identification of peptides that bind to the constant region of a humanized IgG1 monoclonal antibody using phage display, *J. Mol. Recognit.* 11, 121-125
8. Ehrlich, G. K. et al. (2000) Phage display technology. Identification of peptides as model ligands for affinity chromatography, *Methods Mol. Biol.* 147, 209-220
9. Kay, B. K. et al. (2000) Convergent evolution with combinatorial peptides, *FEBS Lett.* 480, 55-62
10. Pasqualini, R. and Ruoslahti, E. (1996) Organ targeting in vivo using phage display peptide libraries, *Nature* 380, 364-366
11. Pasqualini R, et al. (2000) Aminopeptidase N is a receptor for tumor-homing peptides and a target for inhibiting angiogenesis, *Cancer Res,* 60, 722-727
12. Parmley, S. F. and Smith, G. P. (1989) Filamentous fusion phage cloning vectors for the study of epitopes and design of vaccines, *Adv. Exp. Med. Biol.* 251, 215-218
13. Meyer D E, Trabbic-Carlson K, Chilkoti A. (2001) Protein purification by fusion with an environmentally responsive elastin-like polypeptide: effect of polypeptide length on the purification of thioredoxin, *Biotechnol. Prog.* 17, 720-728.
14. Raucher D, Chilkoti A. (2001) Enhanced uptake of a thermally responsive polypeptide by tumor cells in response to its hyperthermia-mediated phase transition, *Cancer Res.* 61, 7163-7170.
15. Yu S M, Conticello V P, Zhang G, Kayser C, Fournier M J, Mason T L, Tirrell D A. (1997) Smectic ordering in solutions and films of a rod-like polymer owing to monodispersity of chain length, *Nature* 389, 167-170.
16. Healy J M, Murayama O, Maeda T, Yoshino K, Sekiguchi K, Kikuchi M. (1995) Peptide ligands for SET alpha v beta 3 selected from random phage display libraries, *Biochemistry* 34, 3948-3955.
17. Kay B K, Kasanov J, Yamabhai M. (2001) Screening phage-displayed combinatorial peptide libraries, *Methods* 24, 240-246.
18. Greenwood, J. et al. (1991) Multiple display of foreign peptides on a filamentous bacteriophage. Peptides from *Plasmodium falciparum* circumsporozoite protein as antigens, *J. Mol. Biol.* 220, 821-827.
19. Fuh G, Pisabarro M T, Li Y, Quan C, Lasky L A, Sidhu S S. (2000) Analysis of PDZ domain-ligand interactions using carboxyl-terminal phage display, *J. Biol. Chem.* 275, 21486-21491.
20. Fuh G, Sidhu S S. (2000) Efficient phage display of polypeptides fused to the carboxy-terminus of the M13 gene-3 minor coat protein, *FEBS Lett.* 480, 231-234.
21. Hyde-DeRuyscher R, Paige L A, Christensen D J, Hyde-DeRuyscher N, Lim A, Fredericks Z L, Kranz J, Gallant P, Zhang J, Rocklage S M, Fowlkes D M, Wendler P A, Hamilton P T. (2000) Detection of small-molecule enzyme inhibitors with peptides isolated from phage-displayed combinatorial peptide libraries. *Chem. Biol.* 7, 17-25.
22. Sparks, A., Adey, N., Cwirla, S. & Kay, B. (1996). Screening phage displayed random peptide libraries. In Phage Display of Peptides and Proteins: A Laboratory Manual. (Kay, B. K., Winter, J. & McCafferty, J., eds), pp 227-254. Academic Press, San Diego.

It is understood that the disclosed invention is not limited to the particular methodology, protocols and reagents described as these may vary. It is also understood that the terminology used herein is for the purposes of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the exemplary methods, devices, and materials are as described. All patents, patent applications and other publications cited herein and the materials for which they are cited are specifically incorporated by reference in their entireties.

Those skilled in the art will recognize, or be able to ascertain using no more than routine experimentation, many equivalents to the specific embodiments of the invention described herein. Such equivalents are intended to be encompassed by the following claims.

We claim:

1. A method of decreasing an activity of SET comprising contacting SET with an ApoE peptide, wherein the activity of SET is inhibition of Protein Phosphatase 2A (PP2A) and/or increasing the activity of Cyclin-Dependent Kinase 5 (CDK5), and wherein the ApoE peptide is capable of binding to SET and consists of the amino acid sequence of SEQ ID NO: 1 or SEQ ID NO: 2, and wherein the activity of SET is decreased upon contact with the ApoE peptide.

2. The method of claim 1, wherein said peptide consists of the amino acid sequence of SEQ ID NO: 1.

3. The method of claim 1, wherein said peptide consists of the amino acid sequence of SEQ ID NO: 2.

4. The method of claim 1, wherein administration of the ApoE peptide reduces phosphorylated p38 Mitogen Activated Protein (MAP) kinase.

5. The method of claim 1, wherein administration of the ApoE peptide reduces LPS-induced nitric oxide.

6. The method of claim 1, wherein administration of the ApoE peptide increases phosphatase activity of PP2A.

7. The method of claim 1, wherein administration of the ApoE peptide reduces Jcasp-induced cell death.

8. The method of claim 1, wherein administration of the ApoE peptide reduces kinase activity of CDK5.

9. A method of identifying an agent that binds to SET and decreases SET activity, comprising contacting SET with at least one test agent to identify one or more agents that bind to SET, and screening said one or more agents for the ability to compete with or inhibit binding of a peptide consisting of the amino acid sequence of SEQ ID NO: 1 to SET, wherein the activity of SET is inhibition of Protein Phosphatase 2A (PP2A) and/or increasing the activity of Cyclin-Dependent Kinase 5 (CDK5).

10. The method of claim 9, further comprising isolating one or more agents that compete with or inhibit binding of a peptide consisting of the amino acid sequence of SEQ ID NO: 1 to SET.

11. The method of claim 10, further comprising
screening said one or more agents for the ability to increase phosphatase activity of PP2A.

12. The method of claim 10, further comprising screening said one or more agents for the ability to decrease kinase activity of CDK5.

* * * * *